United States Patent
Kasic, II

(10) Patent No.: US 9,668,720 B2
(45) Date of Patent: Jun. 6, 2017

(54) SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES

(71) Applicant: DNP Biomed, LLC, Boulder, CO (US)

(72) Inventor: James F Kasic, II, Boulder, CO (US)

(73) Assignee: DNP Biomed, LLC, Boulder, CO (US)

( * ) Notice: Subject to any disclaimer, the term of this patent is extended or adjusted under 35 U.S.C. 154(b) by 0 days.

(21) Appl. No.: 14/887,313

(22) Filed: Oct. 19, 2015

(65) Prior Publication Data

US 2017/0105715 A1 Apr. 20, 2017

(51) Int. Cl.
| | | |
|---|---|---|
| A61B 18/02 | (2006.01) | |
| A61M 29/00 | (2006.01) | |
| A61B 17/02 | (2006.01) | |
| A61B 17/00 | (2006.01) | |
| A61B 18/14 | (2006.01) | |

(Continued)

(52) U.S. Cl.
CPC ........ *A61B 17/0218* (2013.01); *A61B 5/0071* (2013.01); *A61B 17/00234* (2013.01); *A61B 18/14* (2013.01); *A61B 2017/00323* (2013.01); *A61B 2018/00351* (2013.01); *A61B 2018/00577* (2013.01); *A61B 2018/00791* (2013.01); *A61B 2018/00982* (2013.01)

(58) Field of Classification Search
CPC .......... A61M 25/0147; A61M 25/0054; A61M 25/0069; A61M 25/007; A61M 2025/0161; A61M 2025/0175; A61B 2018/00023; A61B 2090/0481; A61B 17/0218; A61B 17/00234; A61B 5/0071; A61B 18/14; A61B 2017/00323; A61B 2018/00351; A61B 2018/00577; A61B 2018/00791; A61B 2018/00982
USPC .... 606/21–26, 1, 34, 41; 600/144–151, 120, 600/380, 201–210; 607/112, 129, 133, 607/135
See application file for complete search history.

(56) References Cited

U.S. PATENT DOCUMENTS

| | | | |
|---|---|---|---|
| 6,067,990 A | * | 5/2000 | Kieturakis ......... A61B 17/0218 128/898 |
| 6,438,400 B1 | | 8/2002 | Beard et al. |
| 7,621,908 B2 | | 11/2009 | Miller |

(Continued)

OTHER PUBLICATIONS

C. Palaniswamy et al., Effectiveness of Esophageal Mechanical Deviation during AF Ablation, PO01-83, Hearty Rhythm Society, May 13, 2015.

(Continued)

*Primary Examiner* — Pedro Philogene
(74) *Attorney, Agent, or Firm* — Woods Patent Law, P.A.

(57) ABSTRACT

Disclosed are various embodiments of systems, devices, components and methods for re-positioning or displacing a patient's esophagus a safe distance away from the patient's heart during an atrial ablation surgical procedure. An esophageal displacement catheter is disclosed that is configured to reposition a patient's esophagus 20 mm or more away from the ablation location in the patient's heart. The catheter is easy to use, and according to some embodiments may be configured to transmit torque on substantially a 1:1 basis between its proximal and distal ends if a distendable section of the catheter needs to be re-positioned in the patient's esophagus.

27 Claims, 19 Drawing Sheets

(51) Int. Cl.
 *A61B 5/00* (2006.01)
 *A61B 18/00* (2006.01)

(56) References Cited

U.S. PATENT DOCUMENTS

| | | |
|---|---|---|
| 7,819,817 B2 | 10/2010 | Rahn |
| 8,224,422 B2 | 7/2012 | Mottola et al. |
| 8,273,016 B2 | 9/2012 | O'Sullivan |
| 8,454,588 B2 * | 6/2013 | Rieker .............. A61M 25/0147 606/191 |
| 8,968,332 B2 * | 3/2015 | Farritor .............. A61B 1/00158 606/1 |
| 2004/0138700 A1 | 7/2004 | Cooper et al. |
| 2007/0118097 A1 | 5/2007 | Miller |
| 2007/0135803 A1 * | 6/2007 | Belson ............... A61B 1/00154 606/1 |
| 2007/0225701 A1 | 9/2007 | O'Sullivan |
| 2008/0033415 A1 | 2/2008 | Rieker et al. |
| 2008/0215047 A1 | 9/2008 | Calabro et al. |
| 2010/0030098 A1 | 2/2010 | Fojtik |
| 2010/0179537 A1 | 7/2010 | Rashidi |

OTHER PUBLICATIONS

Lemola, et al., Computed Tomographic Analysis of the Anatomy of the Left Atrium, Circulation, 2004, pp. 3655-3660.
Musat et al., Computational Method to Predict Esophageal Temperature Elevations During Pulmonary Vein Isolation, PACE, vol. 33, Issue 10, 2010, pp. 1239-1248.
Singh et al., Esophageal Injury and Temperature Monitoring During Atrial Fibrillation Ablation, Circ Arrhythmia Electrophysiol, Aug. 2008, pp. 162-168.

* cited by examiner

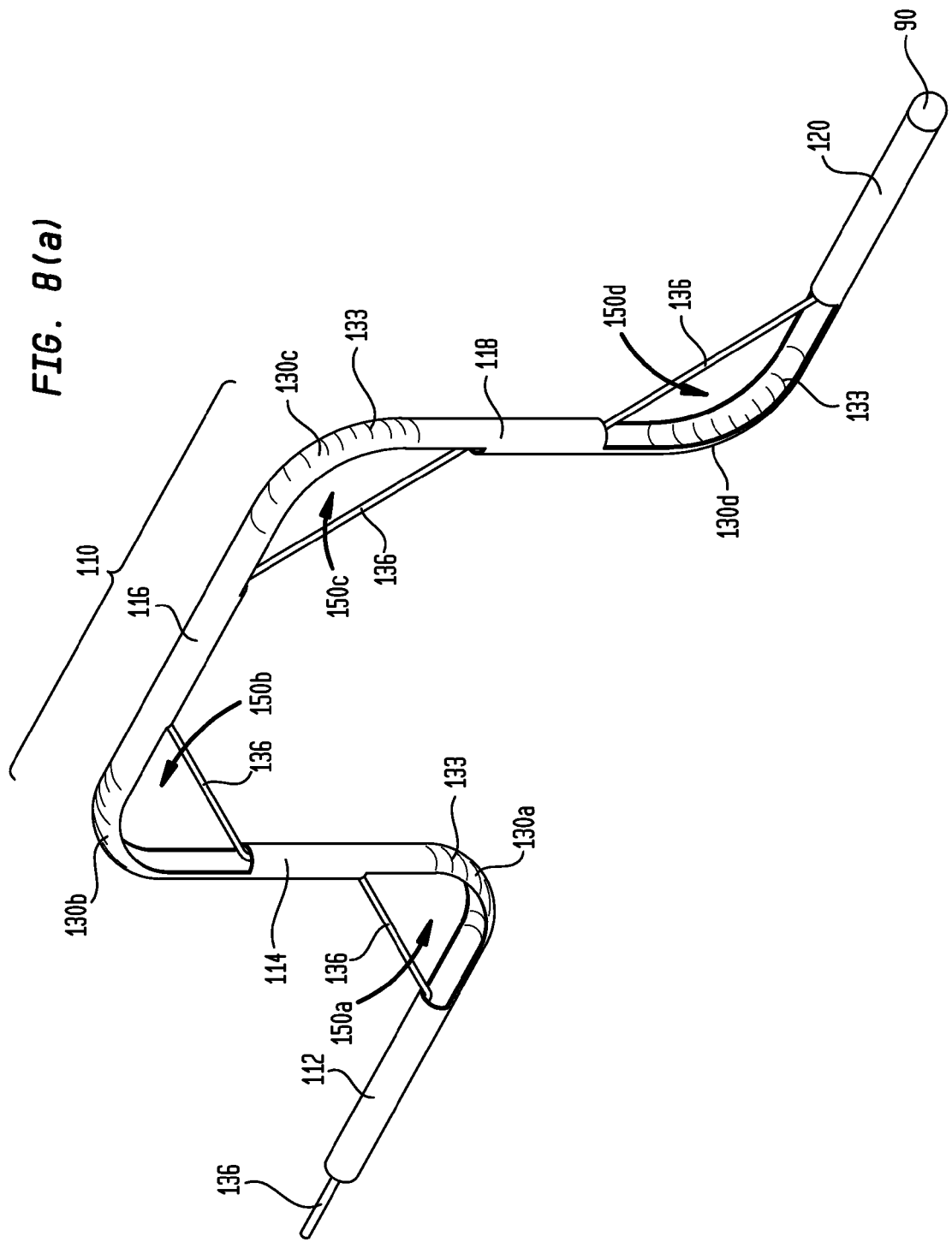

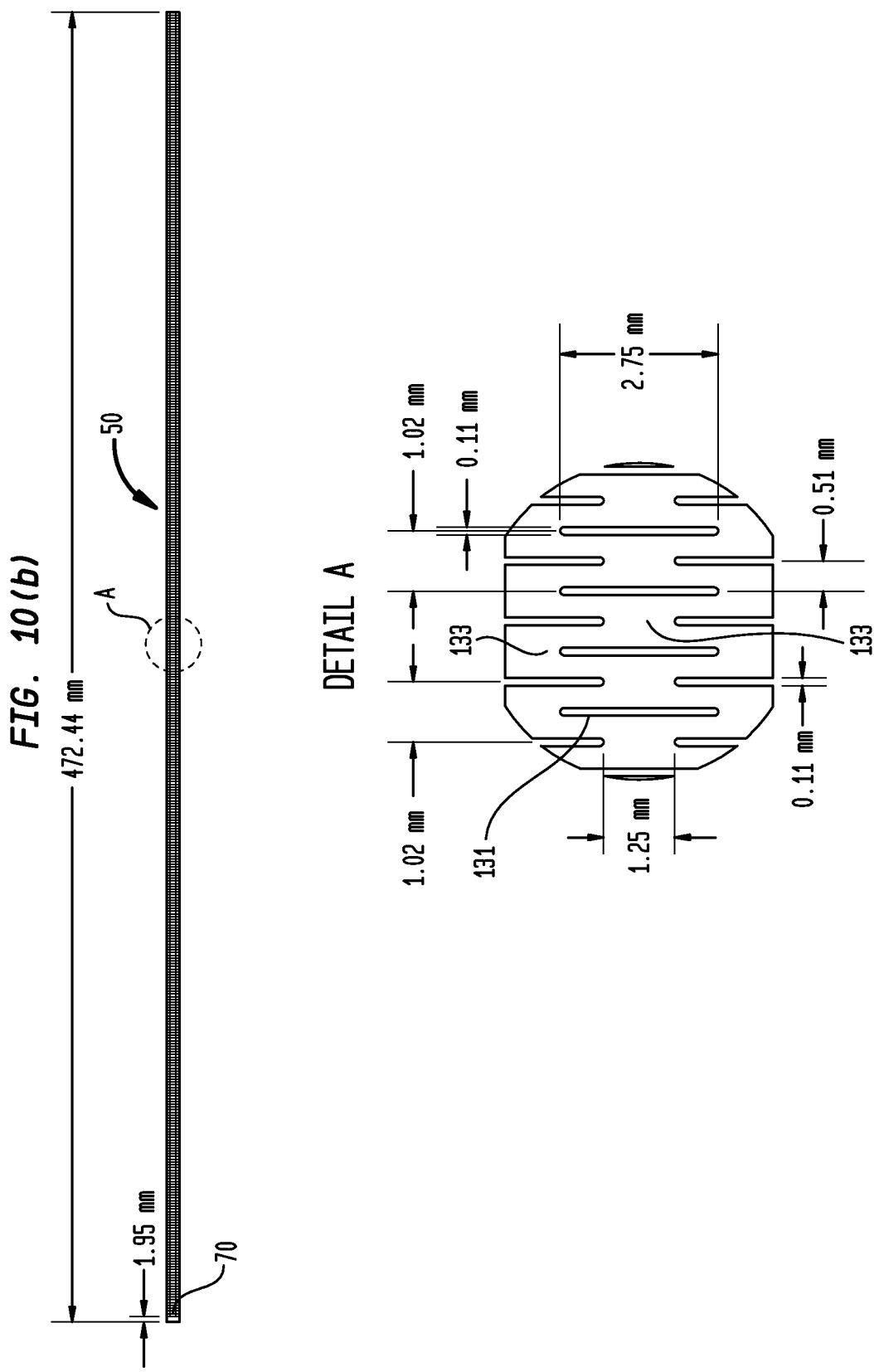

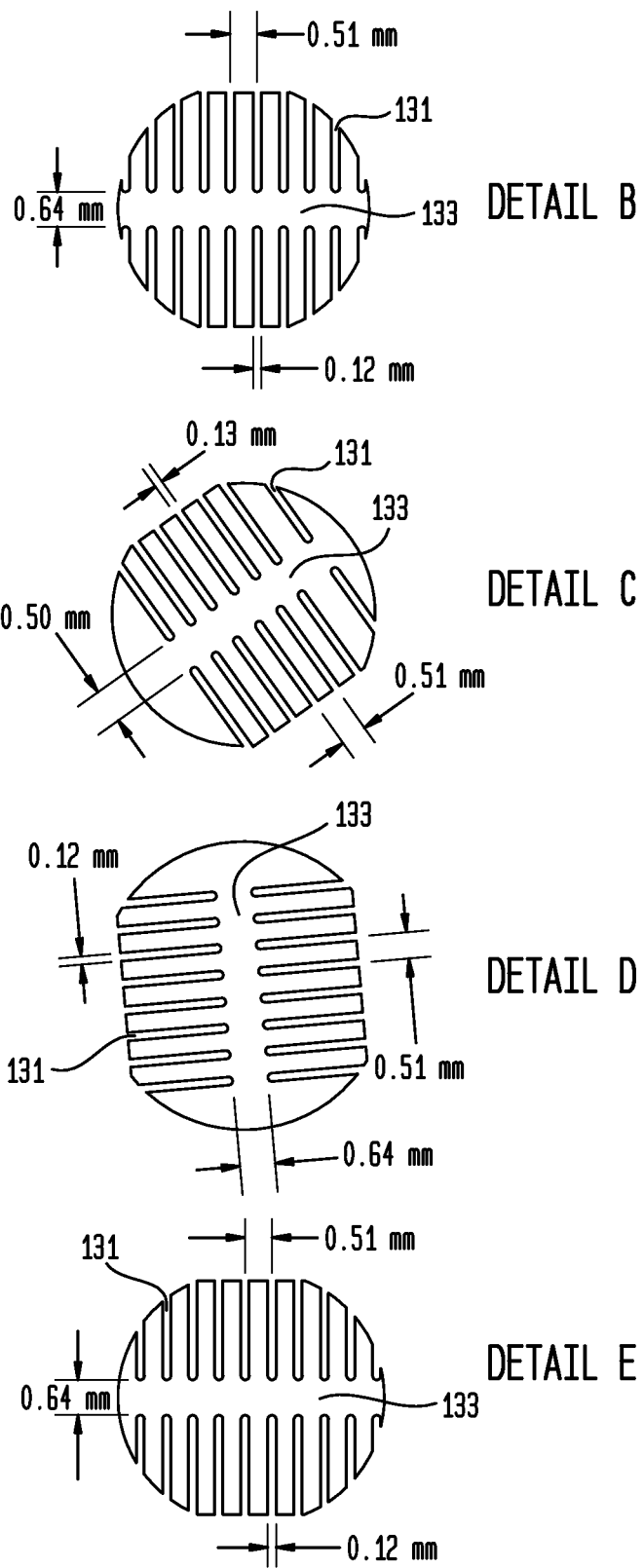

SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES

FIELD OF THE INVENTION

Various embodiments of the invention described herein relate to the field of systems, devices, components, and methods for displacing or repositioning a patient's esophagus away from the patient's heart during an atrial ablation or other surgical procedure.

BACKGROUND

Catheter ablation is commonly employed to treat atrial fibrillation, where errant electrical conductivity pathways in a patient's heart are burned or ablated with the tip of an ablation catheter that is positioned within the patient's atrium during a cardiac ablation surgical procedure. A significant risk in such a procedure is burning or ablating through a wall of the patient's atrium and then into the patient's esophagus. Burning or ablating the patient's esophagus can result in near-immediate death.

Mechanical esophageal displacement of the esophagus away from the heart during a cardiac ablation surgical procedure is therefore highly desirable so that in the event a patient's atrial wall is penetrated during the procedure the esophagus will not be burned or ablated. See "Mechanical Esophageal Displacement during Catheter Ablation for Atrial Fibrillation" by Koruth et al. Journal of Cardiovascular Electrophysiology, Vol. 23, No. 2, February, 2012.

Various devices and methods have been proposed to displace or reposition a patient's esophagus during atrial ablation surgical procedures, many of which suffer from various shortcomings.

What is needed is an esophageal displacement or re-positioning device that is relatively quick and easy to use, and that is capable of reliably re-positioning a patient's esophagus a safe distance away from the patient's heart during a cardiac ablation surgical procedure.

SUMMARY

In one embodiment, there is provided an esophageal displacement catheter comprising a catheter body comprising at least a first lumen, a distal end, a proximal end, and a distendable section, the first lumen extending between at least portions of the proximal and distal ends of the catheter body, the catheter body being configured to assume a substantially straight configuration along a first longitudinal axis, or to assume a flexible or limp configuration at least along portions thereof, when the catheter body is in a relaxed or non-active configuration, a catheter manipulation mechanism disposed at or near the proximal end of the catheter body, at least a first pulling member disposed at least partially within the catheter and the lumen and having a distal portion thereof attached to a portion of the catheter body located at or near the distal end of the catheter body, the pulling member being operably connected to the catheter manipulation mechanism such that a user can tighten and relax the pulling member using a pulling member tightening and loosening mechanism forming a portion of or attached to the catheter manipulation mechanism, wherein the distendable section comprises a plurality of joints and is configured to permit the distendable section to deflect away from the first longitudinal axis and bend substantially within a single plane along a plurality of joints when the pulling member is pulled towards the proximal end of the catheter body, the distendable section and the catheter body further being configured to rotate within substantially the single plane when the proximal end of the catheter body is rotated by a user, and the catheter body is configured such that the distendable section thereof is configured to assume a distended configuration suitable for displacing and repositioning an esophagus of a patient a suitable distance away from the patient's heart when the pulling member is in an active or distended position within the lumen and catheter body as the pulling member is tightened by the user manipulating the catheter manipulation mechanism, and further wherein the catheter is configured such that a torsional and rotational force applied to the proximal end of the catheter body or the catheter manipulation mechanism by the user resulting in a rotation of the proximal end of the catheter body through a prescribed angle determined by the user results in the torsional force being transmitted efficiently through the catheter body and the distendable section such that the distendable section also rotates substantially through the prescribed angle when the torsional and rotational force is applied.

In another embodiment, there is provided a method of displacing a portion of an esophagus of a patient away from the patient's heart with an esophageal displacement catheter, the catheter comprising a catheter body comprising at least a first lumen, a distal end, a proximal end, and a distendable section, the first lumen extending between at least portions of the proximal and distal ends of the catheter body, the catheter body being configured to assume a substantially straight configuration along a first longitudinal axis, or to assume a flexible or limp configuration at least along portions thereof, when the catheter body is in a relaxed or non-active configuration, a catheter manipulation mechanism disposed at or near the proximal end of the catheter body, at least a first pulling member disposed at least partially within the catheter and the lumen and having a distal portion thereof attached to a portion of the catheter body located at or near the distal end of the catheter body, the pulling member being operably connected to the catheter manipulation mechanism such that a user can tighten and relax the pulling member using a pulling member tightening and loosening mechanism forming a portion of or attached to the catheter manipulation mechanism, wherein the distendable section comprises a plurality of joints and is configured to permit the distendable section to deflect away from the first longitudinal axis and bend substantially within a single plane along a plurality of joints when the pulling member is pulled towards the proximal end of the catheter body, the distendable section and the catheter body further being configured to rotate within substantially the single plane when the proximal end of the catheter body is rotated by a user, and the catheter body is configured such that the distendable section thereof is configured to assume a distended configuration suitable for displacing and repositioning an esophagus of a patient a suitable distance away from the patient's heart when the pulling member is in an active or distended position within the lumen and catheter body as the pulling member is tightened by the user manipulating the catheter manipulation mechanism, and further wherein the catheter is configured such that a torsional and rotational force applied to the proximal end of the catheter body or the catheter manipulation mechanism by the user resulting in a rotation of the proximal end of the catheter body through a prescribed angle determined by the user results in the torsional force being transmitted efficiently through the catheter body and the distendable section such that the distendable section also rotates substantially through the prescribed angle when the torsional and rotational force is applied, the method comprising inserting the distal end of the catheter body in the patient's nose or mouth, inserting and positioning the distal end of the catheter into the patient's esophagus, and causing the first pulling member to retract in the direction of the proximal end of the catheter body such that the distendable section is deployed, the distendable section assumes the distended configuration, and the distendable section positions the patient's esophagus away from the patient's heart.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

FIG. 8(a) shows a top perspective view of yet another embodiment of a distendable section 110 of an esophageal displacement and repositioning catheter 10;

FIG. 10(b) shows a side view of catheter body 50 of esophageal displacement and repositioning catheter 10 shown in FIG. 10(a), including detail A thereof;

FIG. 10(e) shows details C, D, E and F of distendable section 110 of esophageal displacement and repositioning catheter 10 shown in FIGS. 10(c) and 10(d);

The drawings are not necessarily to scale. Like numbers refer to like parts or steps throughout the drawings.

DETAILED DESCRIPTIONS OF SOME EMBODIMENTS

Figure 1:
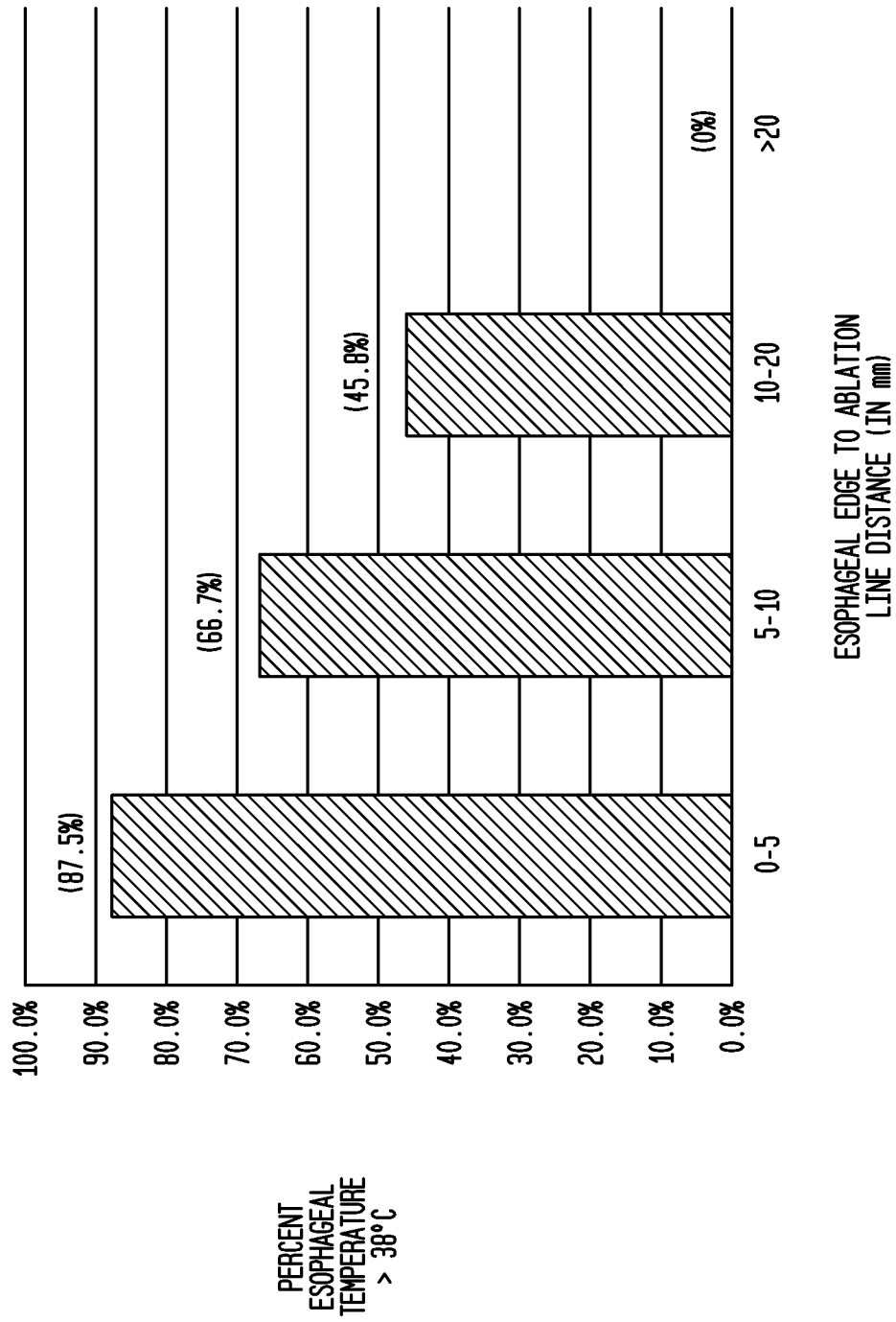
FIG. 1 shows the relationship between esophageal temperature and esophageal edge to ablation line distance in millimeters.

Described herein are various embodiments of systems, devices, components and methods for repositioning and displacing a patient's esophagus away from the patient's heart during an atrial ablation surgical procedure.

The esophagus is in close proximity to the posterior wall of the left atrium, which renders it susceptible to thermal injury during radiofrequency (RF) ablation procedures for atrial fibrillation (AF). Real-time assessment of esophageal position and temperature (T°) during pulmonary vein (PV) isolation has not been extensively explored. See "*Computational Method to Predict Esophageal Temperature Elevations During Pulmonary Vein Isolation*" to Musat, M. D. et al., Pacing and Clinical Electrophysiology, Volume 33, Issue 10, pages 1239-1248, October 2010. Atrial fibrillation ablation (AF ablation) can include isolation of the left or right pulmonary veins by applying ablation energy at their junction with the atrium.

The Centers for Disease Control (CDC) estimates that 12 million people in the US have atrial fibrillation (AF). Worldwide, about 260,000 people are treated by AF ablation each year. In up to 1% of these cases, atrio-esophageal fistulas develop because of overheating and damage that have occurred to the esophagus during the AF ablation procedure. Overheating and damage to the esophagus can occur when heart tissue is burned or ablated through during the AF ablation procedure. Between 70 and 100% of patients who develop atrio-esophageal fistulas as a consequence of AF ablation die. Moreover, esophageal injury of some sort occurs in up to 36% of AF ablation procedures. See "*Computed Tomographic Analysis of the Anatomy of the Left Atrium*" to Lemola et al., Circulation, 2004; and "Esophageal Injury and Temperature Monitoring" to Singh et al., Circulation, October, 2008.

Temperature sensors disposed in the esophagus have been used with varying success during AF ablation procedures, but can be unwieldy, slow to react, have small sensing areas, or be located away from the critically important trailing edge of the esophagus, which is located closest to the site where AF ablation occurs and is therefore most susceptible to damage and overheating.

Various studies have indicated there is little to no heating of the esophagus during an AF ablation procedure when the esophagus is repositioned or displaced at least 20 mm away from the ablation site. See, for example, "*Effectiveness of Esophageal Mechanical Deviation during AF Ablation,*" C. Palaniswamy et al., PO01-83, Hearty Rhythm Society, May 13, 2015

As a result, solutions have focused on moving the esophagus away from the patient's heart during AF ablation procedures using devices such as wires, balloons and catheters. Such devices, however, often suffer from one or more problems, including excessive cost, an inability to achieve the amount of deflection, displacement or repositioning of the esophagus away from the heart required to prevent burning damage or injury to the esophagus, trauma to the oropharynx, and an inability to rotate or reposition, or difficulty in rotating or repositioning, the device in the esophagus once it has been inserted in the esophagus and deployed. For example, many balloon- and catheter-based devices are incapable of transmitting torque efficiently or adequately between the proximal and distal ends thereof if fluoroscopic or other suitable imaging techniques reveal that the device must be rotated in the esophagus to achieve the desired amount of esophageal displacement away from the heart. Moreover, the location of the trailing edge of the esophagus (which is closest to the ablation site and therefore most susceptible to burning or injury) is typically not taken into account by the various esophageal displacement devices that have been developed. See "Mechanical Esophageal Displacement During Catheter Ablation for Atrial Fibrillation," J. Koruth et al., Journal of Cardiovascular Electrophysiology, Volume 23, Issue 2, pages 147-154, February 2012.

The various embodiments disclosed and described herein provide solutions to at least some of the problems outlined above.

Referring now to the Figures, in FIG. 1 there are shown measured relationships between esophageal temperature and an esophageal edge-to-ablation line distance in millimeters. FIG. 1 is adapted from C. Palaniswamy et al., Heart Rhythm Scientific Sessions, 2015, in Boston, Mass. (see above), and illustrates the importance of re-positioning or displacing the esophagus, generally in a lateral direction instead of a posterior direction, and typically 20 mm or more away from the ablation site during an AF ablation procedure. FIG. 1 illustrates the percentage of patients where the edge of the esophagus was heated to a temperature exceeding 38 degrees Celsius as a function of distance between the esophagus and the ablation site. As shown, no patients experienced heating of the edge of the esophagus above 38 degrees Celsius when the distance between the edge of the esophagus and the ablation site exceeded 20 mm.

Figure 2A:
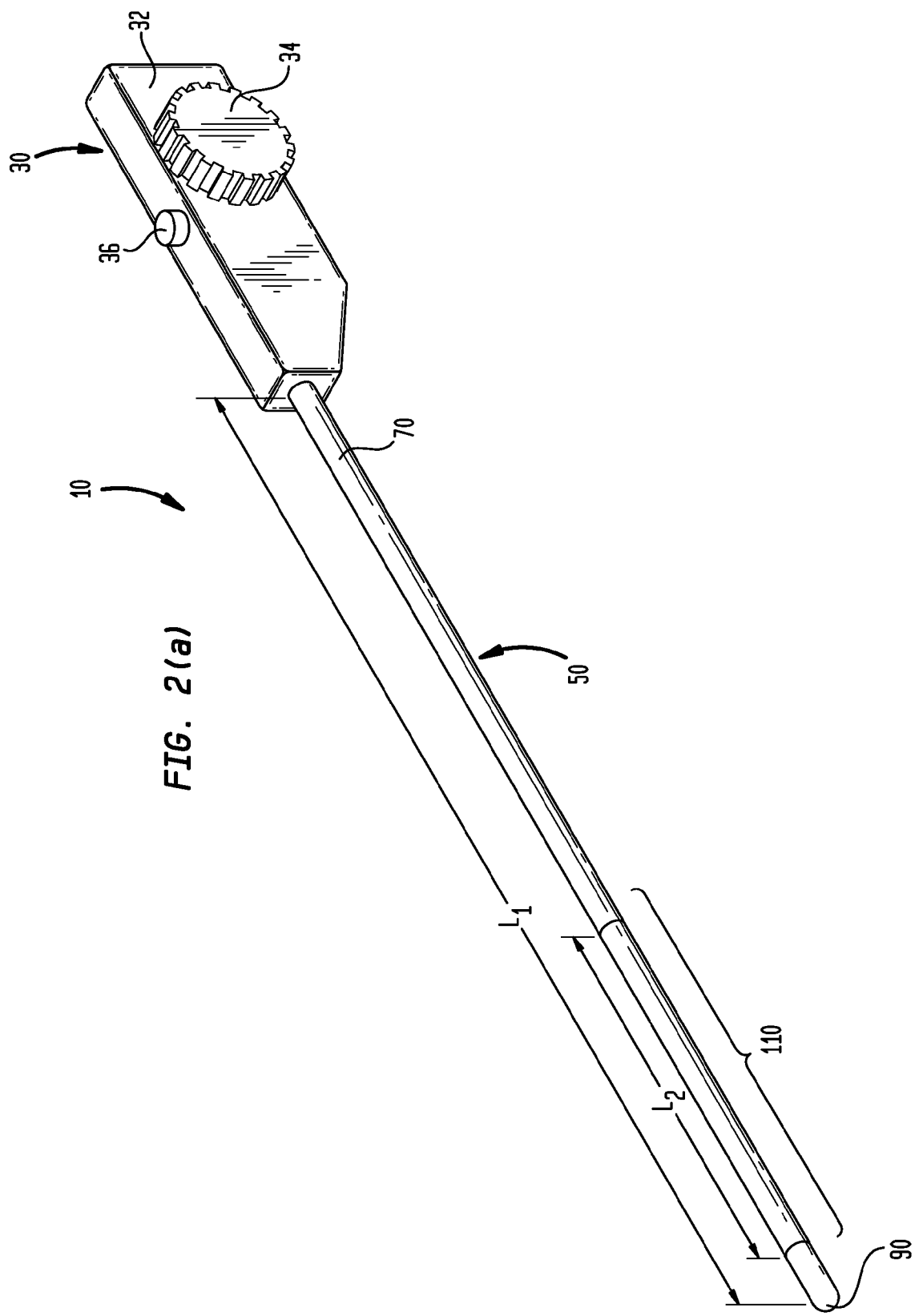
FIG. 2(a) shows a top perspective view of one embodiment of an esophageal displacement and repositioning catheter 10 in a resting or non-distended position.

FIG. 2(a) shows a top perspective view of one embodiment of an esophageal displacement and repositioning catheter 10 in a resting or non-distended position. As shown, catheter 10 comprises catheter body 50 having proximal end 70 and distal end 90, distendable section 110 of catheter body 50, and catheter manipulation handle 30. Catheter body 50 is further characterized in having overall length L1, and length L3 associated with distendable section 110. In one embodiment, catheter manipulation mechanism or handle 30 comprises housing 32, pulling member tightening and loosening dial 34, and ratchet locking and unlocking button 36. Other types of pulling member tightening and loosening mechanisms known to those skilled in the art are also contemplated, such as triggers, levers, and so on.

Figure 2B:
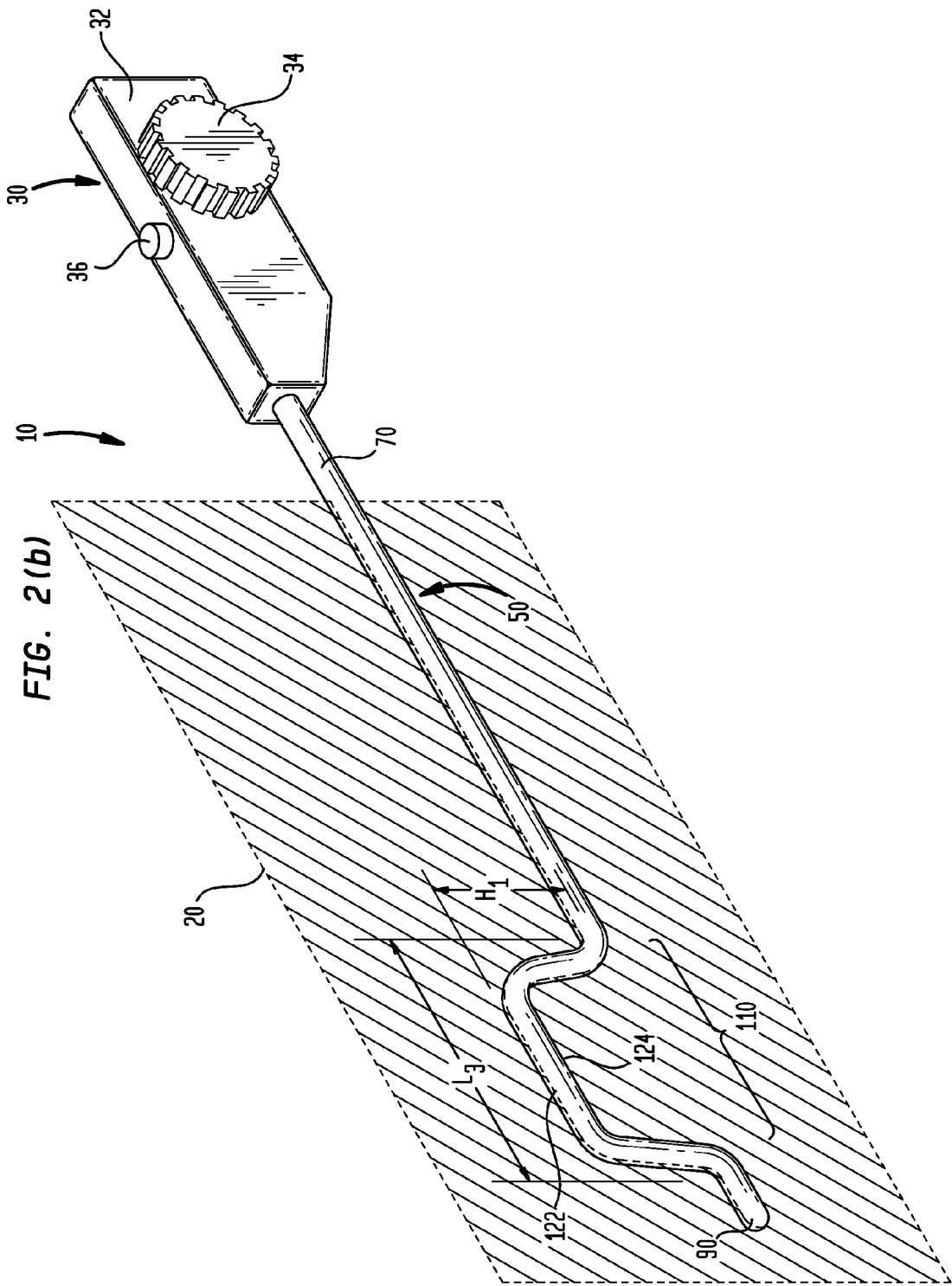
FIG. 2(b) shows a top perspective view of the esophageal displacement and repositioning catheter 10 of FIG. 2(a) in an active or distended position.

FIG. 2(b) shows a top perspective view of esophageal displacement and repositioning catheter 10 of FIG. 2(b), where distendable section 110 is in an active or distended position, and where a user or health care provider has employed handle 30 and dial 34 to retract a first pulling member 136 (not shown in FIGS. 2(a) through 2(c), but described in further detail below and in other Figures) disposed within catheter body 50 thereby to cause distendable section 110 to assume the distended configuration shown in FIG. 2(b). As shown, distendable section 110 comprises a leading edge 122 and a trailing edge 124, and a first height H1.

Catheter body 50 of FIGS. 2(a) through 2(c) also comprises at least a first lumen 40 (also not shown in FIGS. 2(a) through 2(c), but described in further detail below and in other Figures), which is configured to accommodate first pulling member 136, and which extends between at least portions of proximal and distal ends 70 and 90.1n one embodiment, the at least first pulling member 136 is disposed at least partially within catheter body 50 and lumen 40. A plurality of substantially rigid segments located in or on a distendable section of catheter 10, where the segments are serially connected to one another by flexible joints, are disposed in distendable section 110 (more about which is said below and shown in other figures). Each of such segments is rotatable through a prescribed range of angles, and the segments are configured to rotate within substantially a same plane thereby to transmit rotational torque efficiently through distendable section 110. Other rigid sections can be connected proximally from distendable section 110 to handle 30 or proximal end 70 thereby to transmit rotational torque efficiently from proximal end 70 to distal end 90 through distendable catheter body 50.

Figure 2C:
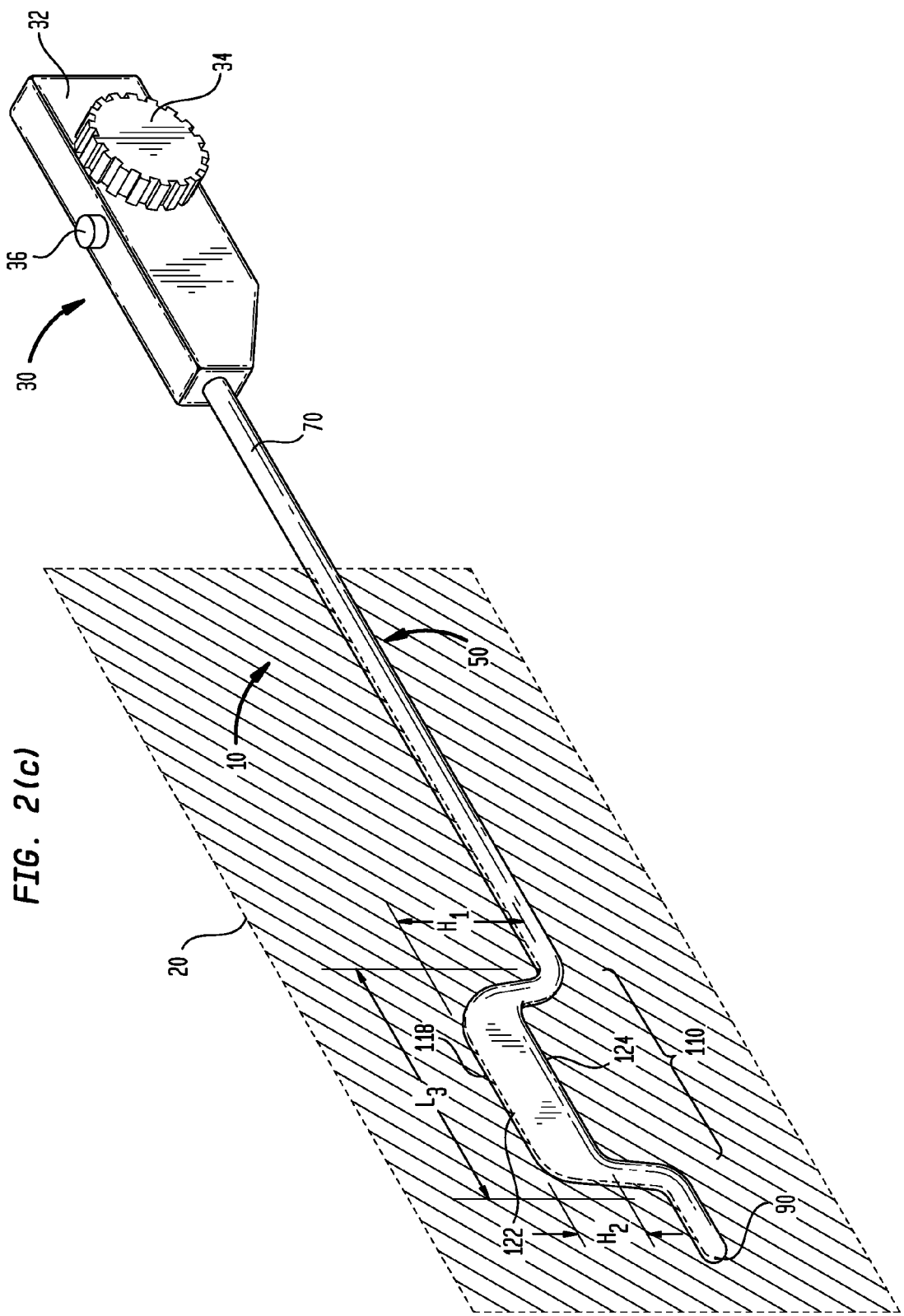
FIG. 2(c) shows a top perspective view of another embodiment of an esophageal displacement and repositioning catheter 10 in an active or distended position.

Additionally, shown in FIGS. 2(b) and 2(c) is imaginary or single plane 20, which bisects catheter body 50 and distendable section 110 when distendable section 110 is distended, deployed or activated. Distendable section 110 comprises a plurality joints and is configured to deflect away from a longitudinal axis associated with the remaining undeflected portion of catheter body 50. In the distended configuration, distendable section 110 bends and deflects substantially within single plane 20 along the plurality of joints when pulling member 136 is pulled towards proximal end 70 of catheter body 50. Distendable section 110 and catheter body 50 are further configured to rotate substantially within single plane 20 when the proximal end 70 of catheter body 50 or catheter manipulation mechanism 30 is rotated by a user. Catheter body 50 is configured such that distendable section 110 is configured to assume a distended configuration (shown in FIGS. 2(b) and 2(c) suitable for displacing and repositioning an esophagus of a patient a suitable distance away from the patient's heart (e.g., 20 mm or more away from the patient's heart) when the pulling member is in an active or distended position within lumen 40 and catheter body 50 as pulling member 136 is tightened by the user manipulating the catheter manipulation mechanism or handle 30. In addition, catheter 50 is configured such that a torsional and rotational force applied to proximal end 70 of catheter body 50 or catheter manipulation mechanism 30 by the user results in a rotation of proximal end 70 of catheter body 50 through a prescribed angle determined by the user, and also results in such torsional force being transmitted efficiently through catheter body 50 and distendable section 110 such that distendable section 110 also rotates substantially through the prescribed angle when the torsional and rotational force is applied by the user.

Thus, in the embodiments shown in FIGS. 2(a) through 2(c), catheter 10 is configured to be substantially straight and/or at least partially flexible or limp between proximal and distal ends 70 and 90 when first pulling member 136 is in a resting or non-distension position within lumen 40, and catheter 10 is further configured such that distendable section 110 thereof assumes a distended configuration suitable for displacing and repositioning an esophagus of a patient away from the patient's heart when first pulling member 136 is in an active or distended position within lumen 40 and catheter body 50 as first pulling member 136 is pulled by a user using, by way of non-limited example, catheter manipulation mechanism or handle 30. In addition, and in one embodiment, catheter 10 is configured such that a rotational or torsional force applied to proximal end 70 of catheter body 50 or handle 30 results in a rotation of proximal end 70 of catheter body 50 through a prescribed number of degrees and further results in such torsional force being transmitted efficiently through catheter body 50 and distendable section 110 such that distal end 90 of catheter body 50 also rotates substantially through the prescribed number of degrees when the such force is applied by a user or health care provider, distendable section and catheter body 50 rotating together substantially in single plane 20.

FIG. 2(c) shows a top perspective view of another embodiment of an esophageal displacement and repositioning catheter 10 in an active or distended position. As shown, catheter 10 comprises catheter body 50 having proximal end 70 and distal end 90, distendable section 110 of catheter body 50, and catheter manipulation handle 30. Catheter body 50 is further characterized in having length L3 associated with distendable section 110, and heights H1 and H2 associated with distendable section 110. Handle 30 comprises housing 32, pulling member tightening and loosening dial 34, and ratchet locking and unlocking button 36. In the embodiment shown in FIG. 2(c), distendable section 110 is in an active or distended position, where a user or health care provider has employed handle 30 and dial 34 to retract a first pulling member 136 (not shown in FIG. 2(c), but described in further detail below and in other Figures) disposed within catheter body 50 thereby to cause distendable section 110 to assume the distended configuration shown in FIG. 2(c). As shown, distendable section 110 comprises a leading edge 122 and a trailing edge 124, a first height H1, and a second height H2. In comparison to the embodiment of FIGS. 2(a) and 2(b), it will be seen that distendable section 110 of the embodiment shown in FIG. 2(c) features a thickened or greater diameter distendable section 110, where leading edge 122 is separated from trialing edge 124 by height H2.

It has been discovered that a thickened or greater diameter distendable section 110 can help pull at least portions of the trailing edge 202 of esophagus 200 (not shown in FIG. 2(c), but described below and shown in other Figures), towards distendable section 110 and therefore a further distance away from a patient's atrium or heart during an AF ablation procedure than can be achieved with the embodiment of catheter 10 shown in FIGS. 2(a) and 2(b).

Referring now to FIGS. 2(a) through 2(c), and in some embodiments, esophageal displacement catheter 10 is characterized by the following dimensions and/or specifications: (a) prescribed ranges of angles between sections of distendable section 110 may range between about 40 degrees and about 90 degrees; (b) first length L1 between proximal and distal ends 70 and 90 of catheter body 50 may range between about 200 mm and about 600 mm; (c) second length L2 of distendable section 110 may range between about 100 mm and about 300 mm; (d) third length L3 of distendable section 110 may range between about 80 mm and about 250 mm (with about 100 mm being a preferred third length L3, according to some embodiments); (e) first height H1 of distendable section 110 may range between about 40 mm and about 140 mm (with about 80 mm being a preferred first height H1 according to some embodiments), and second height H2 of distendable section 110 may range between about 20 mm and about 80 mm. Other dimensions and specifications that will now become apparent to those skilled in the art are also contemplated.

Figure 3:
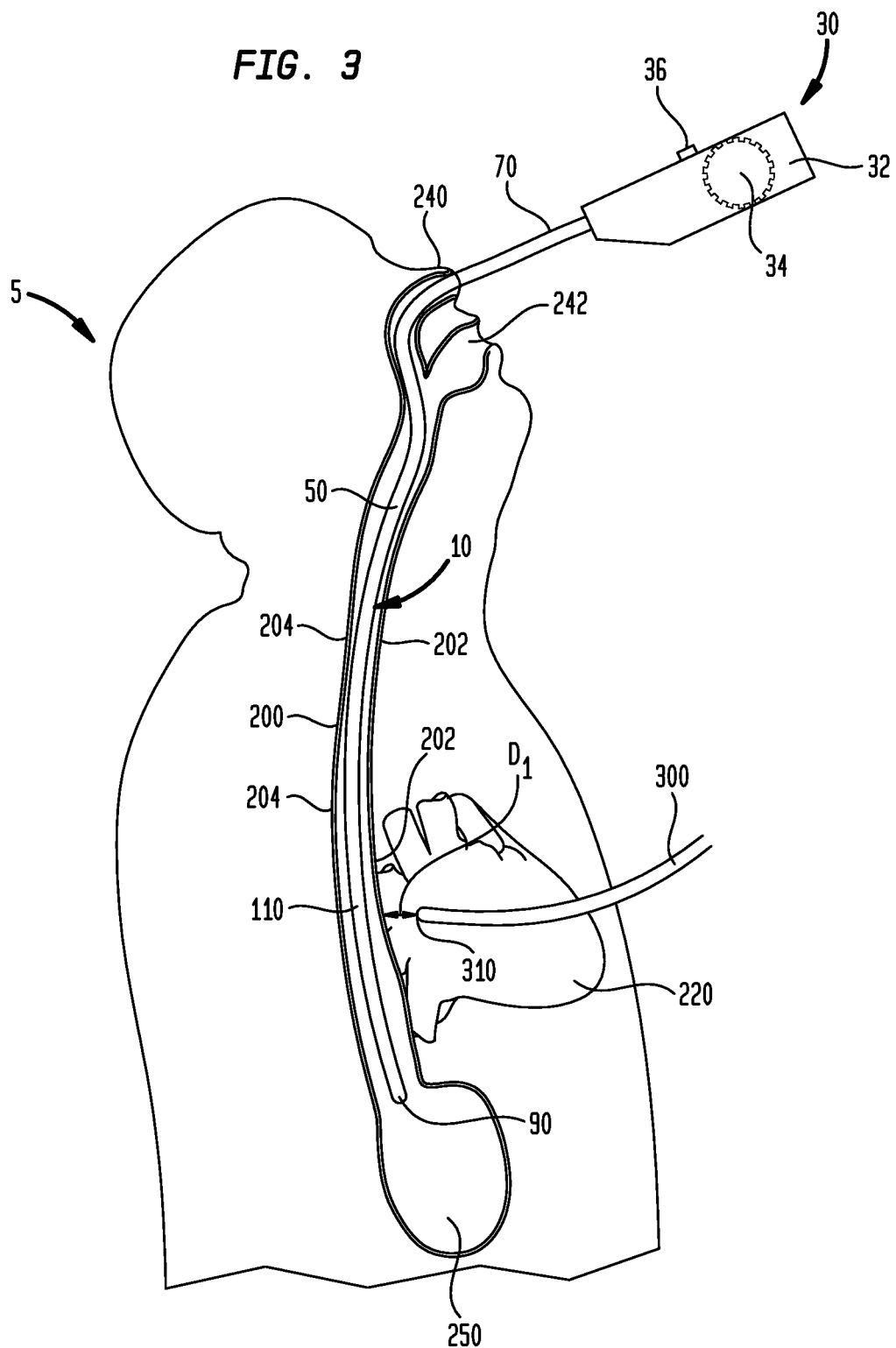
FIG. 3 shows a cross-sectional view of one embodiment of an esophageal displacement and repositioning catheter 10 positioned in esophagus 200 of patient 5, where catheter 10 is in a resting or non-distended position.

FIG. 3 shows a cross-sectional view of one embodiment of esophageal displacement and repositioning catheter 10 positioned in esophagus 200 of a patient 5, where catheter 10 is in a resting or non-distended position in patient 5. Ablation tip 310 of AF ablation catheter 300 is positioned in one of the patient's atria. Trailing edge 202 of esophagus 200 is located in close proximity to, or distance D1 away from, heart 200 and ablation tip 310. Leading edge 204 of esophagus 200 is located further away from ablation tip 310 than distance D1. Catheter 10 can be configured such that catheter body 50 has length L1 such that distal end 90 is configured to enter stomach 250, or is configured not to enter stomach 250. Indeed, catheter 10 can be configured to have lengths L1, L2, L3, L4, H1 and H2 selected such that catheter 10 may be employed successfully in patients of different ages or who have differing esophageal, nose, mouth, and stomach dimensions and morphologies.

In one embodiment, catheter body 50 has a diameter of about 6 mm or less so that it can be inserted through a patient's nose, and further such that the patient need not undergo general anesthetic during the AF ablation procedure (as is typically done when an esophageal catheter is placed through the patient's mouth into esophagus 200).

In addition, esophageal displacement catheter 10 may comprise at least one mark disposed along catheter body 50 indicative of at least one of a first position of distal end 90 of catheter 10 in patient 5's esophagus 200 and a second position of distendable section 110 in the patient 5's esophagus 200. In still other embodiments, esophageal displacement catheter 10 may comprise one or more temperature sensors, ultrasonic transducers, opaque markers, and/or navigation sensors disposed in distendable section 110 or other portions of catheter 10.

Figure 4:
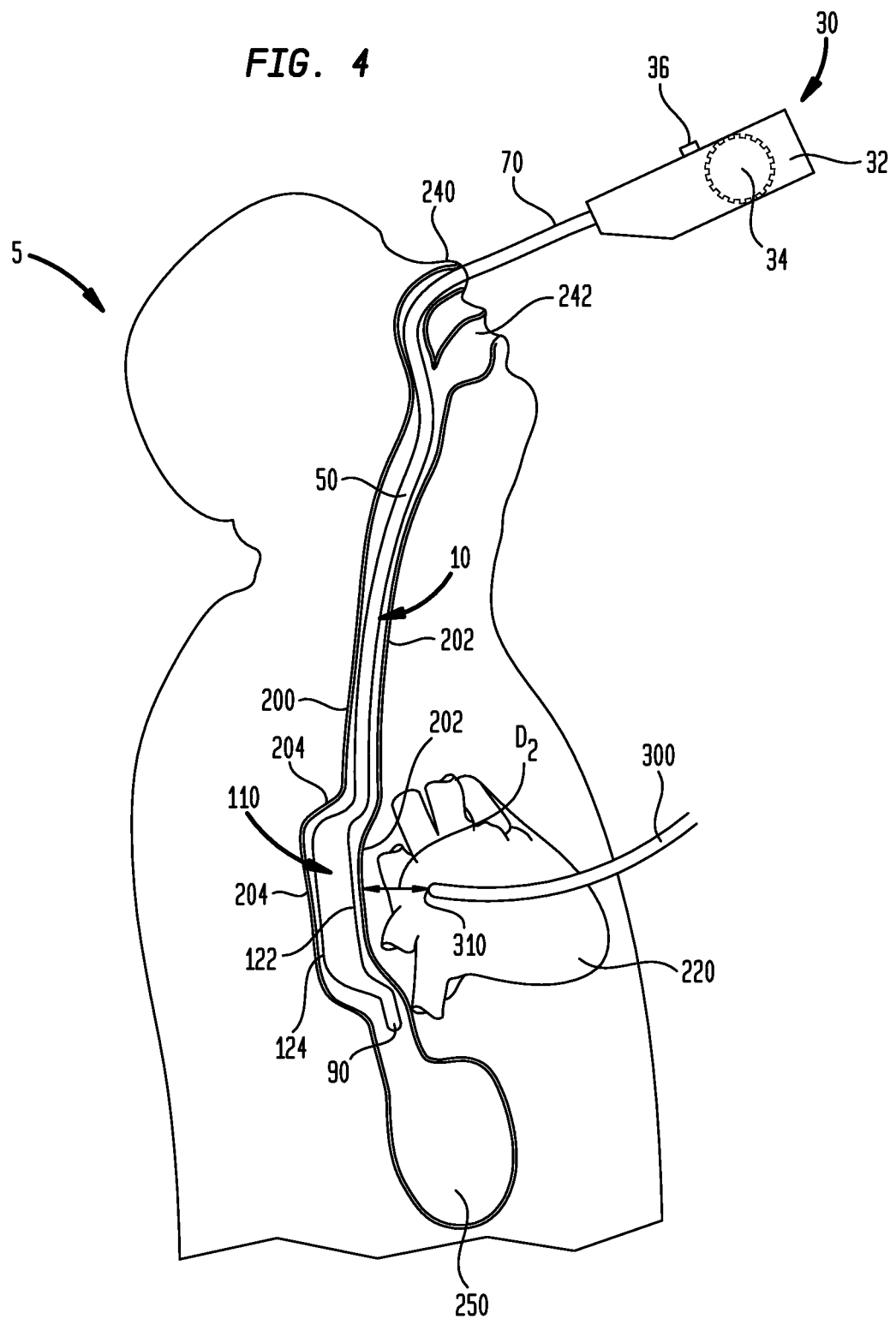
FIG. 4 shows a cross-sectional view of the esophageal displacement and repositioning catheter 10 of FIG. 3 positioned in esophagus 200 of patient 5, where catheter 10 is in an active or distended position.

FIG. 4 shows a cross-sectional view of the esophageal displacement and repositioning catheter 10 of FIG. 3 positioned in esophagus 200 of a patient 5, where catheter distendable section 110 of catheter 10 is in an active or distended position. As shown, trailing edge 204 of esophagus is now located a distance D2 away from ablation tip 310, esophagus 200 having been repositioned or displaced away from heart 220 by distendable section 110 of catheter 10. In some embodiments, catheter 10 and distendable section 110 are configured such that trailing edge 202 of esophagus 200 is located at least about 20 mm away from heart or ablation tip 310, at least about 25 mm away from heart or ablation tip 310, at least about 30 mm away from heart or ablation tip 310, at least about 35 mm away from heart or ablation tip 310, at least about 40 mm away from heart or ablation tip 310, at least about 45 mm away from heart or ablation tip 310, and/or at least about 50 mm away from heart or ablation tip 310. Catheter 10 may also be configured such that Distance D2 achievable by catheter 10 is adjustable or selectable according to a number of pre-selected or predetermined heights H1 and/or H2 that catheter 10 is configured to provide.

Figure 5:
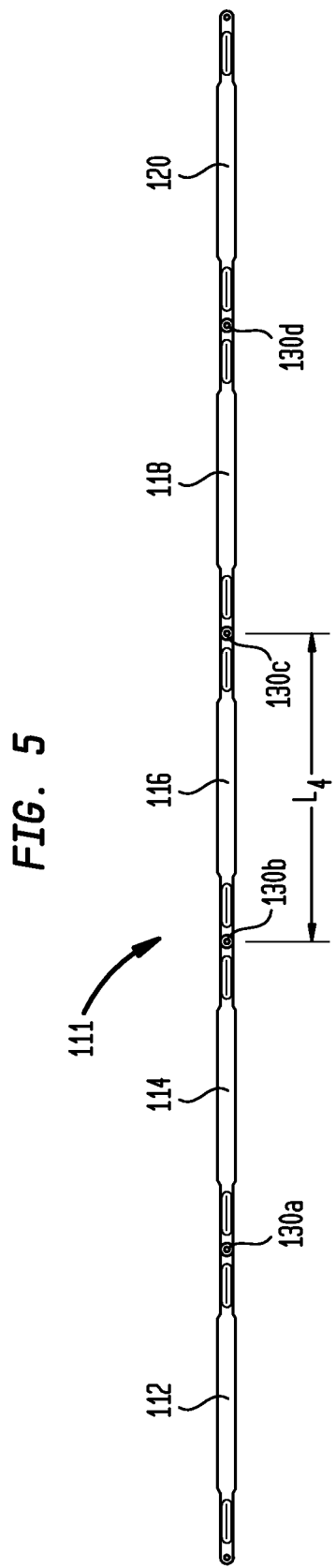
FIG. 5 shows a side view of one embodiment of a portion 111 of a distendable section 110 of an esophageal displacement and repositioning catheter 10.

Referring now to FIG. 5, there is shown a side view of one embodiment of a portion 111 of a distendable section 110 of an esophageal displacement and repositioning catheter, where a plurality of substantially rigid segments 112, 114, 116, 118 and 120 are configured to be located in or on distendable section 110 of catheter 10. As shown, segments 112, 114, 116, 118 and 120 are serially connected to one another by flexible or rotatable joints 130a, 130b, 130c, and 130d, and each of segments 112, 114, 116, 118 and 120 are rotatable through a prescribed range of angles (see FIGS. 6 and 7). Furthermore, segments 112, 114, 116, 118 and 120 are configured to rotate within substantially a same plane such that torque can be efficiently transmitted from a proximal end of distendable section 110 to a distal end of distendable section 110. In one embodiment, segments 112, 114, 116, 118 and 120 are formed, machined or milled from a metal or metal alloy, but may also be formed using suitably stiff plastics, polymers or other materials.

Figure 6:
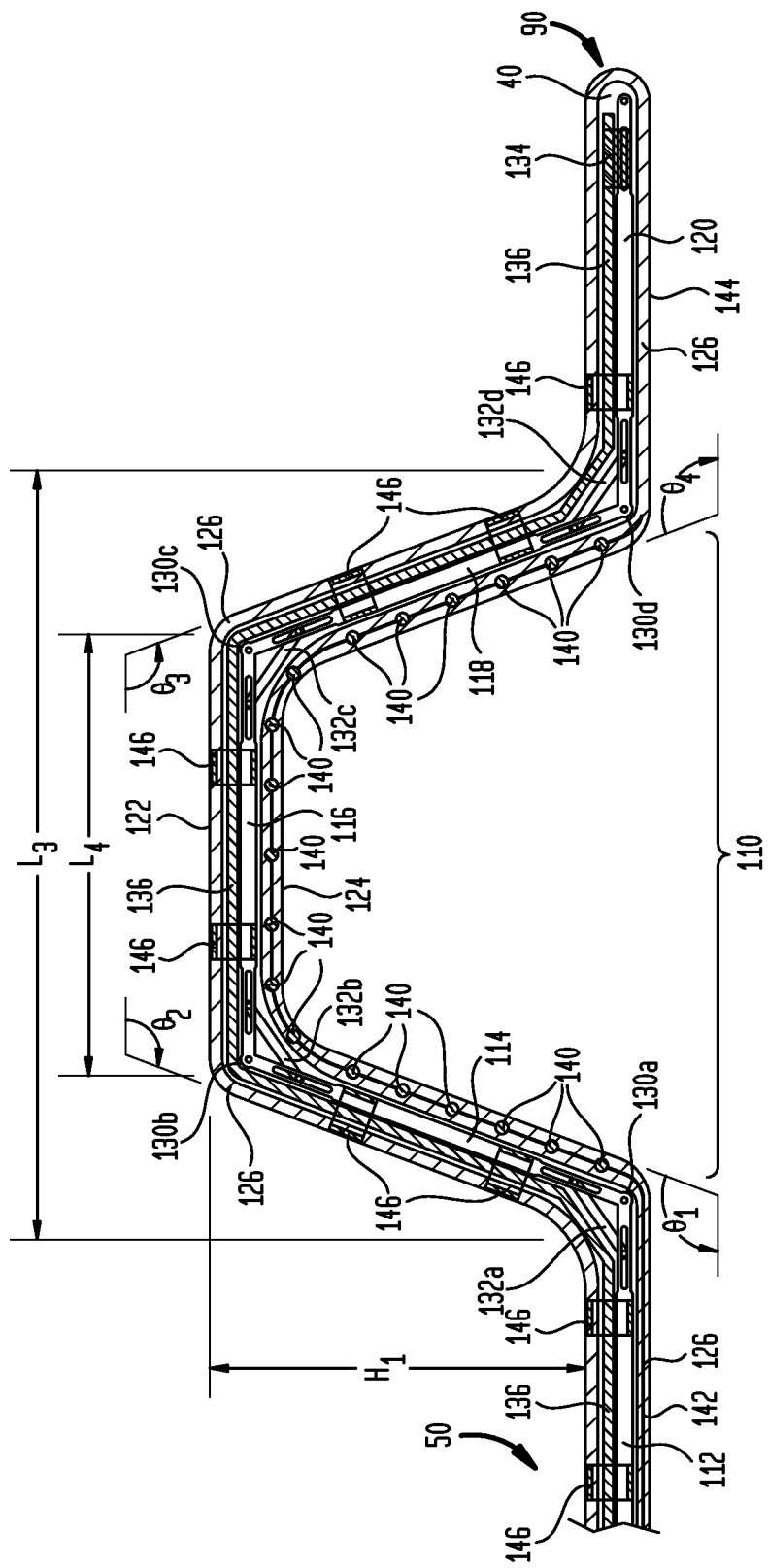
FIG. 6 shows a side cross-sectional view of one embodiment of a distendable section 110 of an esophageal displacement and repositioning catheter 10.
Figure 7:
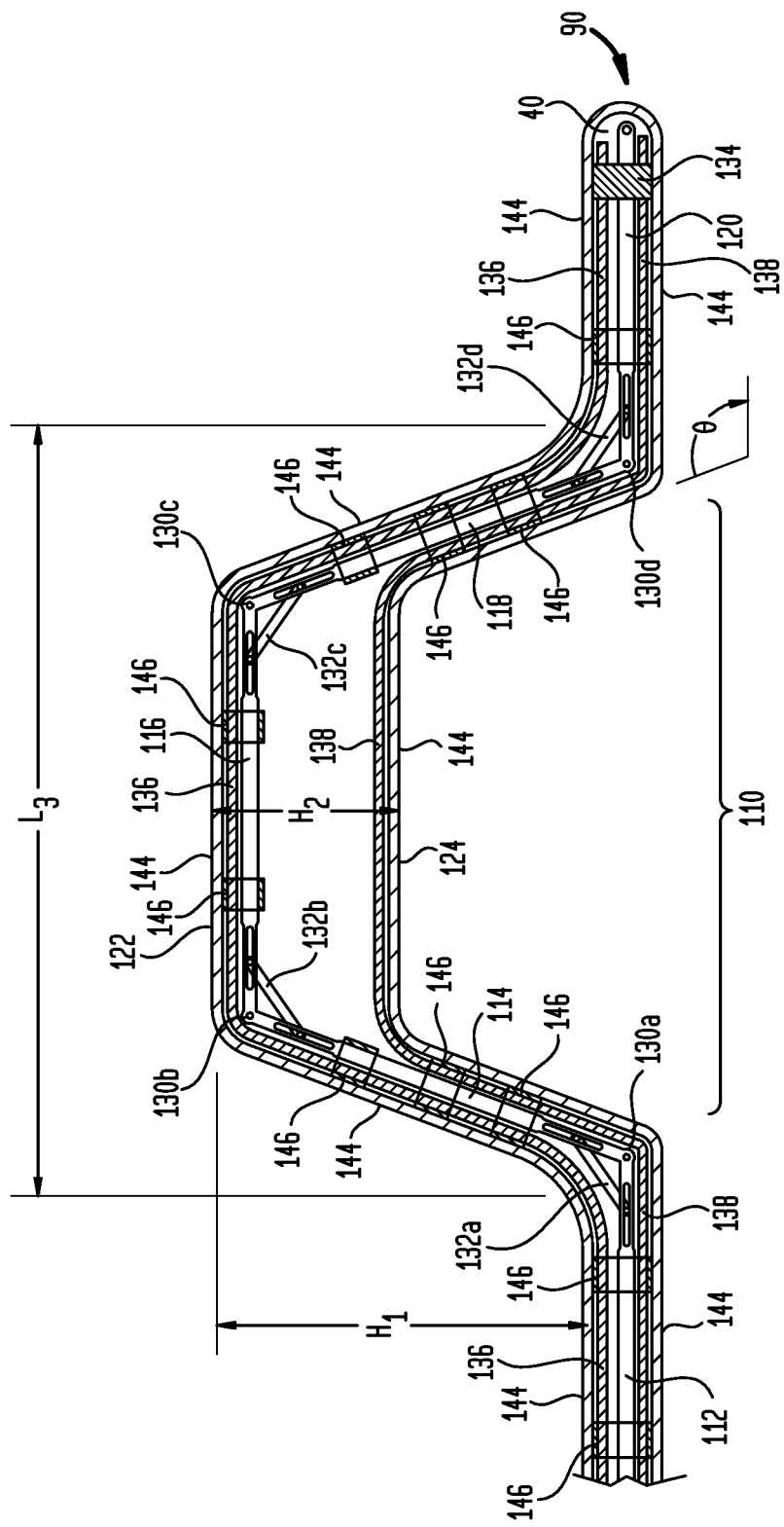
FIG. 7 shows a side cross-sectional view of another embodiment of a distendable section 110 of an esophageal displacement and repositioning catheter 10.

Not shown in FIG. 5, but shown in FIGS. 6 and 7, are range limiters 132a, 132b, 132c, and 132d corresponding to each rotational joint 130a, 130b, 130c, and 130d, respectively, which are configured to prevent the various individual sections of distendable section 110 from over-rotating with respect to one another and potentially causing the collapse of distendable section 110 in an undesired manner. Range limiters 132a through 132d may be configured in a number of different ways, including with wires formed of single, braided or stranded individual wires, strands of synthetic fibers such as KEVLAR™, telescoping members, rigid materials, stretchable or elastic materials, or any other suitable material. Range limiters 132a, 132b, 132c and 132d are configured to prevent over-rotation of joints 130a, 130b, 130c and 130d when first pulling member 136 is retracted in catheter 10.

FIG. 6 shows a side cross-sectional view of one embodiment of distendable section 110 of esophageal displacement and repositioning catheter 10. FIG. 6 shows various details of distendable section 110 not shown in the preceding Figures. Shown in FIG. 6 are elastic, flexible and/or stretchable catheter sheath, covering or outer layer 144, range limiters 132a, 132b, 132c, and 132d, ferrules or stand-offs 146 through which first pulling member 136 slides, first pulling member anchor 134, and substantially rigid sections 112, 114, 116, 118 and 120 disposed in a distended configuration having angles $\theta_1$, $\theta_2$, $\theta_3$, and $\theta_4$ disposed therebetween. These angles are limited by range limiters 132a, 132b, 132c and 132d, respectively. In one embodiment, outer layer 144 is configured to protect esophagus 200 from catheter 50 and pull wire 136, by "sucking" pull wire 136 back into the lumen of catheter 50 (or towards supports 130 or 136). Outer layer 144 can also be configured to insulate any metal or metal alloy incorporated into catheter 50 from patient's esophagus 200 or other portions of the patient's body. In some embodiments, outer layer 144 is formed of silicone or any other suitable flexible elastic material appropriate for use inside a patient's body.

Further shown in FIG. 6 are temperature sensors 140, which according to one embodiment are incorporated into catheter 10 and at least portions of distendable section 110 and sheath, covering or outer layer 144 such that temperatures in the vicinity of distendable section 110 and/or other sections of catheter body 50 may be monitored during an AF ablation procedure. Such temperature sensors 140 may molded into covering, sheath or outer layer 144, or may be provided in any other suitable portion of catheter body 50; corresponding electrical conductors can be provided in catheter 10 to transmit temperature signals to handle 30 from sensors 140. Note that temperature or other navigation or acoustic sensors, transmitters or receivers may be provided external or internal to catheter body along and/or on the outer surface thereof, internal thereto, or in a coating or sheath disposed over catheter 50. Ideally, in those embodiments where temperature sensors 140 are employed, and for purposes of providing the most accurate temperature readings unaffected or substantially unaffected by the thermal properties of the materials from which catheter 50 or coatings or sheaths disposed thereover are formed, temperature sensors 140 are disposed along catheter 50 such that they are positioned near or in close proximity to trailing edge 202 of esophagus 200, and therefore on an outside surface of catheter 50, when catheter 50 is employed to displace esophagus 200 away from ablation site 310. Temperature sensor signals may be transmitted wirelessly from catheter 50 to handle 30 or any other desired reception site (such as an external temperature signal monitoring and amplification device). Similarly, navigation and radio-opaque markers may be disposed along or in catheter body 50 and/or distendable section 110 to permit enhanced imaging of catheter 10 after it has been disposed within a patient 5 by fluoroscopic, computerized tomography (CT) scanning, or any other suitable imaging method.

FIG. 7 shows a side cross-sectional view of another embodiment of distendable section 110 of esophageal displacement and repositioning catheter 10, where second pulling member 138 is further included in catheter 10 and distendable section 110. As shown, second pulling member 138 is configured to be retracted after distendable section 110 has been deployed into a distended configuration by retracting first pulling member 136. Second pulling member 138 then causes elastic or distendable outer sheath or covering 144 to be drawn downwardly from section 116 in the direction of the trailing edge 204 of esophagus 200 (not shown in FIG. 7) such that trailing edge 124 of distendable section 110 located below section 116 may be positioned in closer proximity to trailing edge 204 of esophagus 200. Such positioning of trailing edge 124 of catheter 10 permits more accurate measurements of temperatures in the vicinity of the trailing edge 204 of esophagus 200 (when temperature sensors are provided in or near trailing edge 124, which are not shown in FIG. 7), and also permits at least portions of the trailing edge 204 of esophagus 200 to be drawn more closely to distendable section 110 when deployed inside the patient's esophagus, thereby reducing the risk of burn or injury to the esophagus during an AF ablation procedure.

Figure 8B:
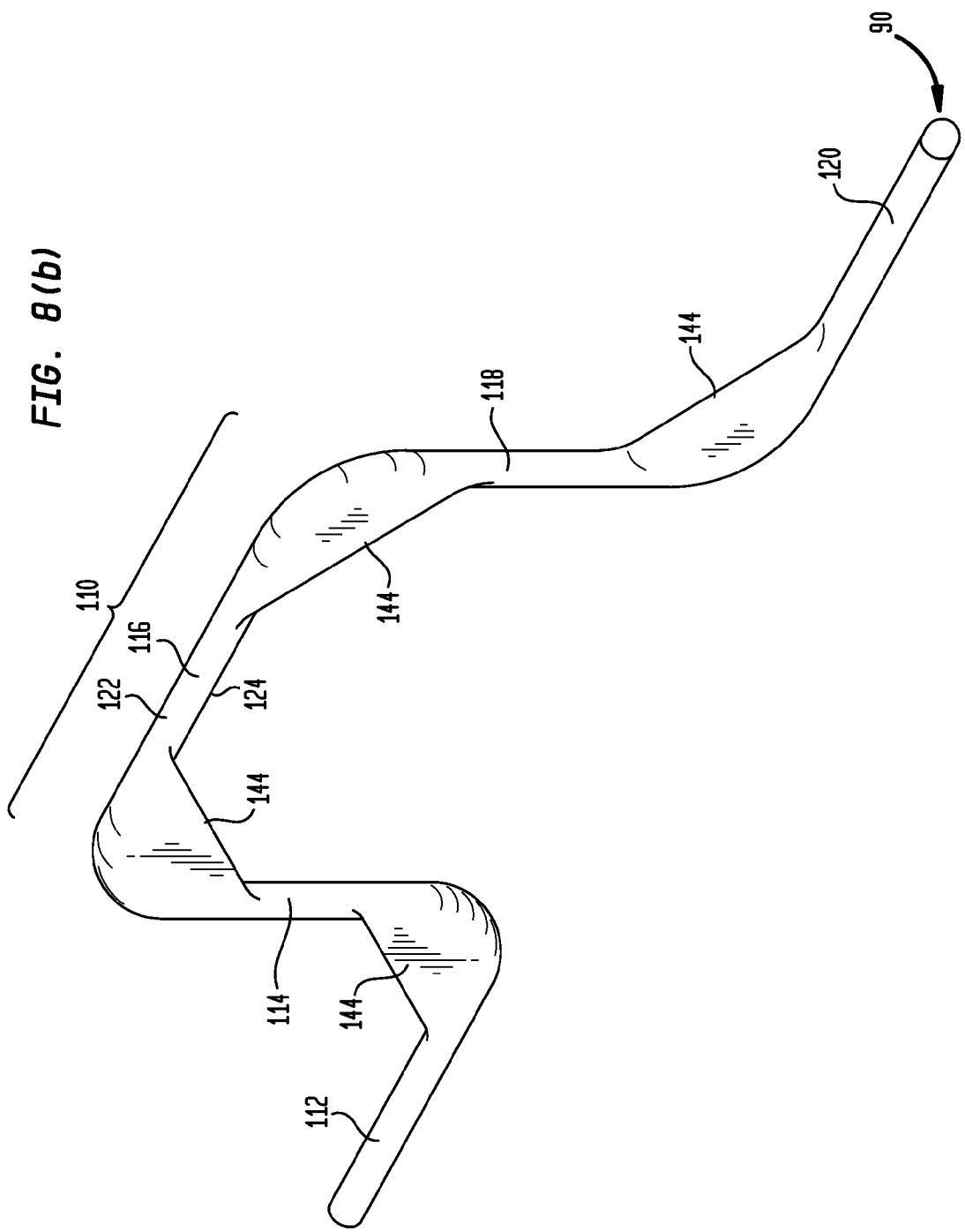
FIG. 8(b) shows distendable section 110 of esophageal displacement and repositioning catheter 10 of FIG. 8(a) having an elastic, flexible or distendable sheath 144 positioned thereover.

FIG. 8(a) shows a top perspective view of yet another embodiment of a distendable section 110 of an esophageal displacement and repositioning catheter 10. In FIG. 8(a), and for purposes of easing illustration and description, outer elastic, distendable, stretchable and/or flexible layer, sheath or covering 144 is not shown (but is shown in FIGS. 8(b) and 8(c)). In addition, and again for purposes of easing illustration and description, range limiters 130a, 130b, 130c and 130d are not shown in FIG. 8(a) (but are shown in FIG. 8(c)). In FIG. 8(a), distendable section 110 comprises a series of sections 112, 114, 116, 118 and 120 that are joined by flexible joints 130a, 130b, 130c and 130d. In one embodiment, sections 112, 114, 116, 118 and 120, and flexible joints 130a, 130b, 130c and 130d, are all formed of thin-walled stainless steel or any other suitable metal, metal alloy, plastic or polymer. Flexible joints can be formed by suitably slitting or cutting distendable section 110 at appropriate locations corresponding to the locations of flexible joints 130a, 130b, 130c and 130d, thereby to form bendable joints 130a, 130b, 130c and 130d, each of which comprises a plurality of slits cut into distendable section 110, where such slits are disposed at suitable locations along distendable section 110, the slits having suitable width and length dimensions to permit a desired amount, degree and type of bending at joints 130a, 130b, 130c and 130d. In some embodiments, the thickness of the sidewalls of sections 112, 114, 116, 118 and 120 can range between about 0.2 mm and about 0.8 mm, and catheter 50 has an overall diameter ranging between about 4 mm and about 10 mm. Diameters of about 6 mm and less for catheter 50 are preferred, as they can more easily be inserted in esophagus 200 through patient's nose 240 (instead of through patient's mouth 242).

Continuing to refer to FIG. 8(a), first pulling member 136 is configured to cause distendable section 110 to assume a distended configuration when retracted through the action of a user or health care provider, and exits distendable section 110 at locations 150a, 150b, 150c, and 150d where recesses are formed in the sidewalls of distendable section 110 opposite flexible joints 130a, 130b, 130c and 130d. Second pulling member 138 is configured to cause trailing edge 124 of outer sheath 144 to be pulled downwardly away from section 116 when retracted through the action of a user or health care provider in a fashion similar to that described above with respect to FIG. 7.

FIG. 8(b) shows distendable section 110 of FIG. 8(a) in a distended configuration, but with flexible, elastic or distendable sheath or covering 144 disposed over the outer surfaces thereof.

Figure 9A:
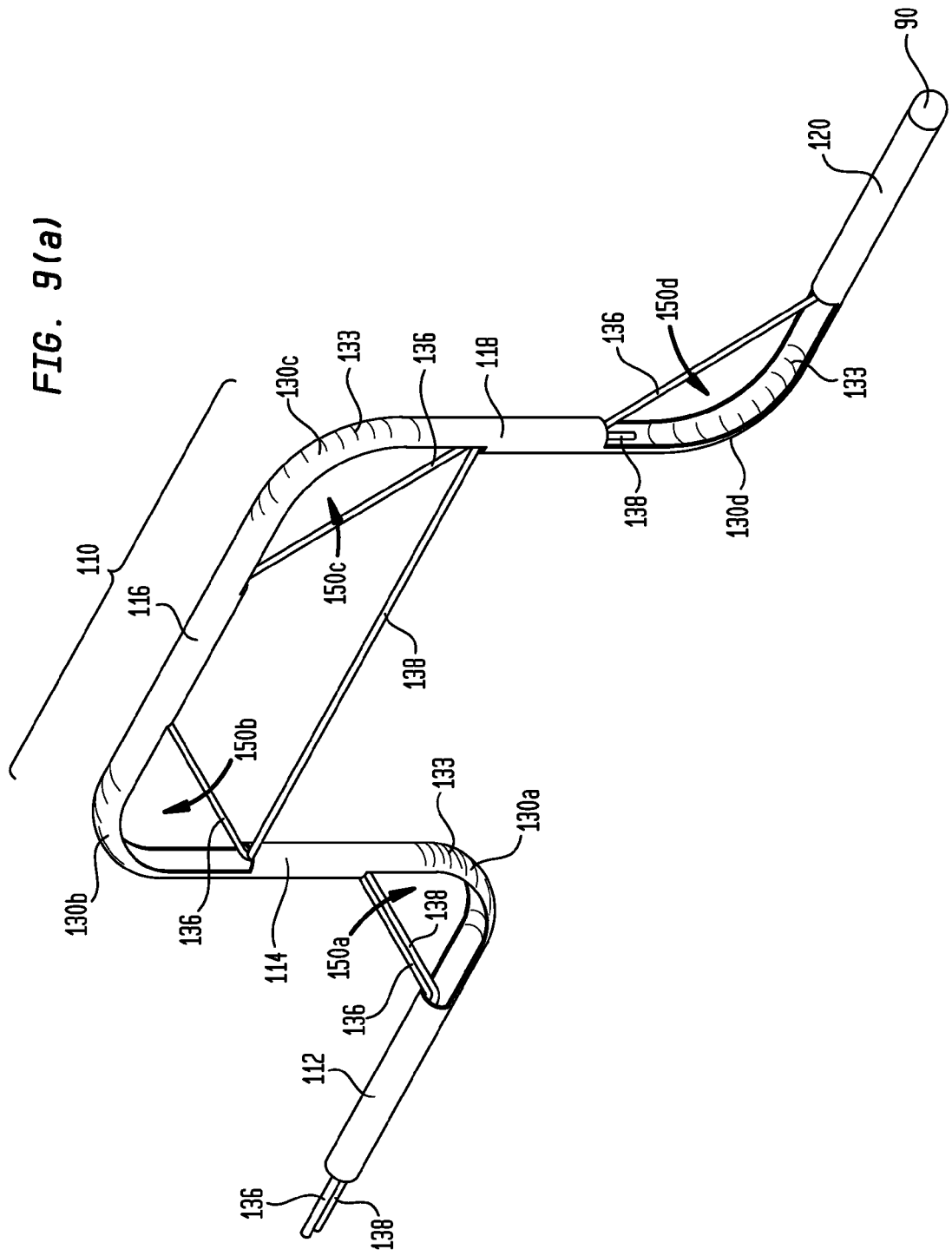
FIG. 9(a) shows a top perspective view of still another embodiment of a distendable section 110 of an esophageal displacement and repositioning catheter 10.
Figure 9B:
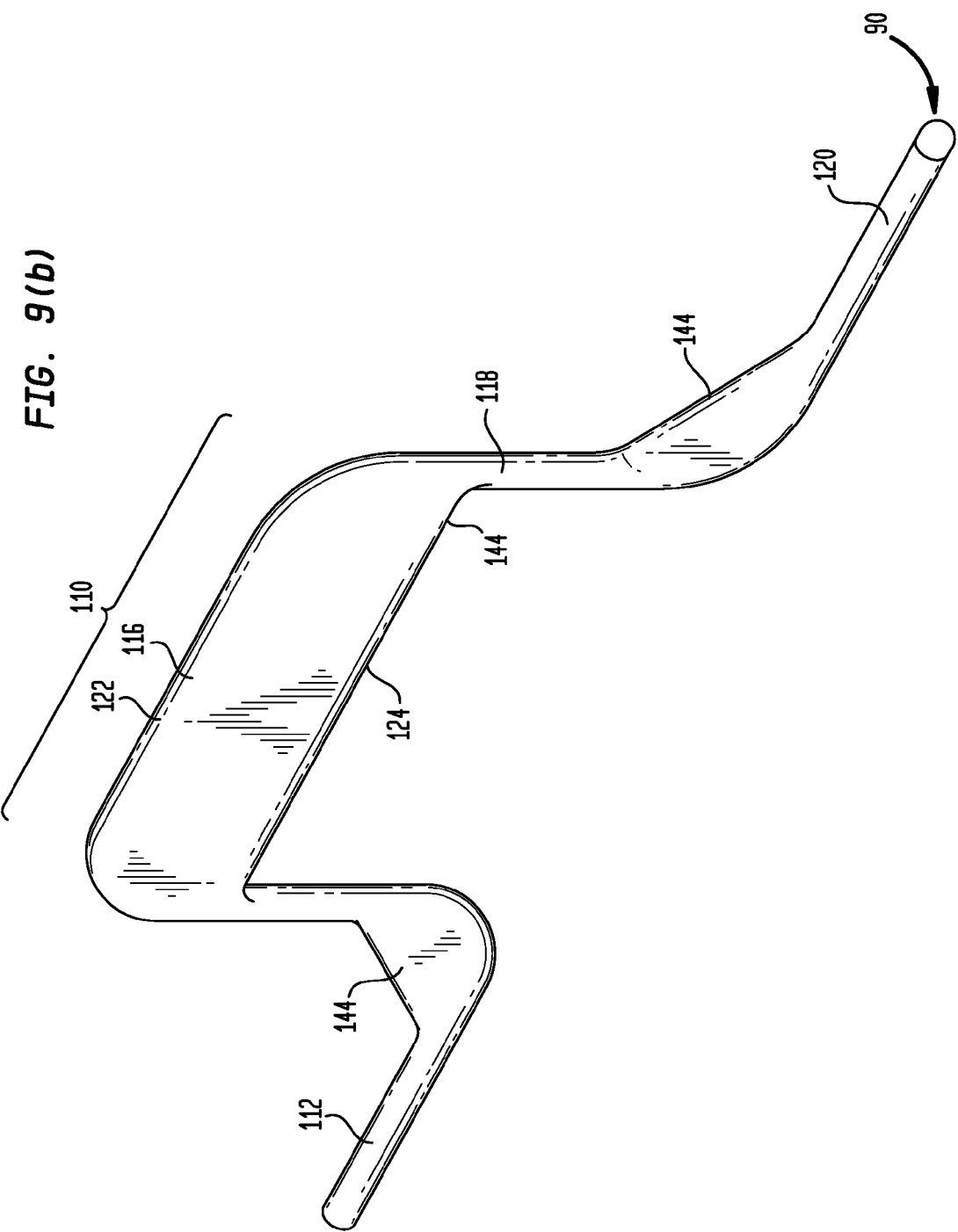
FIG. 9(b) shows distendable section 110 of esophageal displacement and repositioning catheter 10 of FIG. 8(a) having an elastic, flexible or distendable sheath 144 positioned thereover.
Figure 9C:
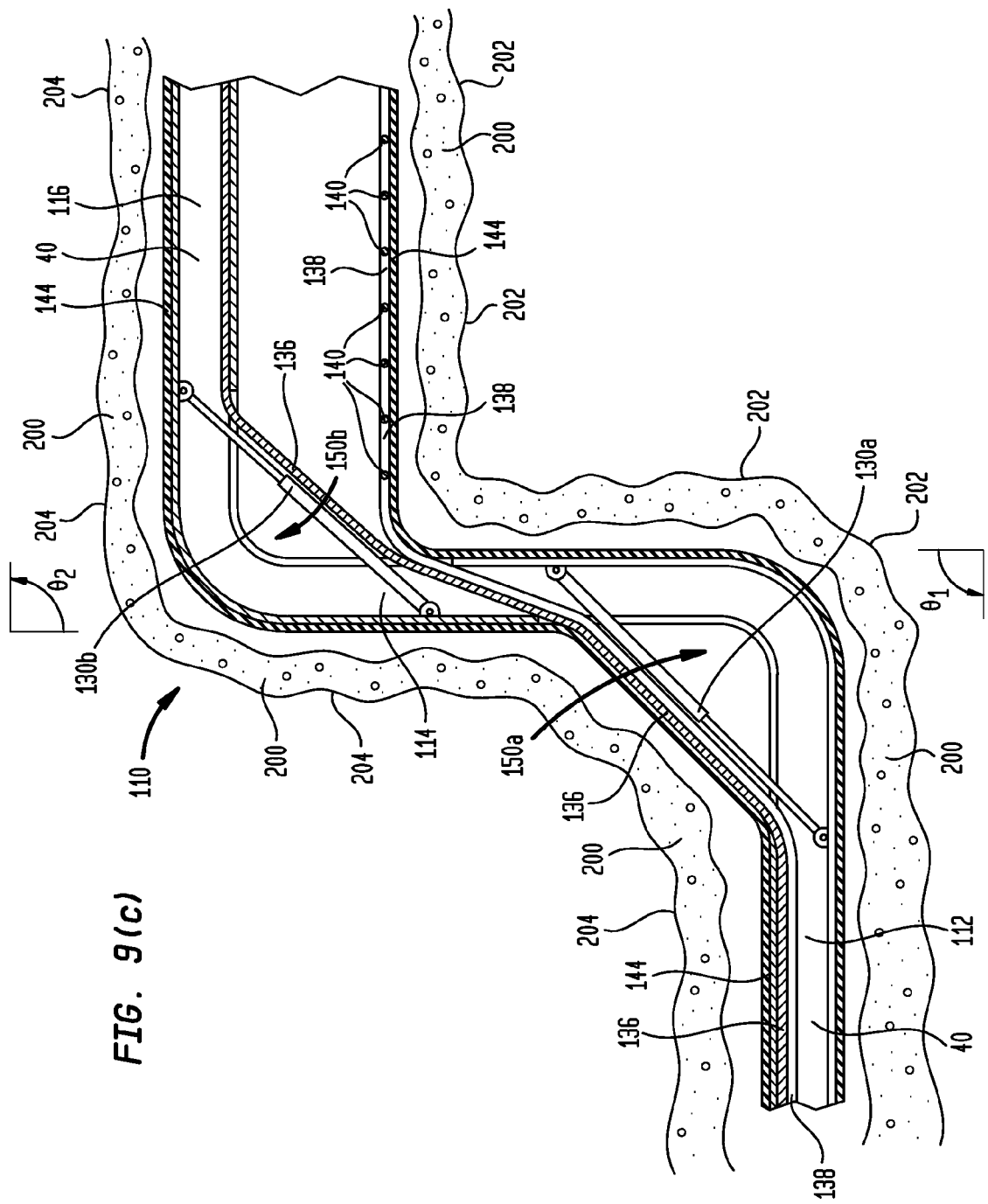
FIG. 9(c) shows a cross-sectional view of a portion of the distendable section of the esophageal displacement and repositioning catheter of FIG. 9(b)

FIG. 9(a) shows a top perspective view of still another embodiment of a distendable section 110 of an esophageal displacement and repositioning catheter 10. FIG. 9(b) shows distendable section 110 of esophageal displacement and repositioning catheter 10 of FIG. 8(a) having an elastic, flexible or distendable sheath 144 positioned thereover. FIG. 9(c) shows a cross-sectional view of a portion of the distendable section of the esophageal displacement and repositioning catheter of FIG. 9(b). Stand-offs 146 guide and restrict the movement of wires 136 and 138 inside lumen 40. Temperature or other sensors or markers 140 are disposed along trailing edge 124, for example to measure esophageal temperature during an AF ablation procedure or permit accurate imaging of the position of catheter 10 in patient 5.

FIGS. 10(a) through 10(e) illustrate certain features according to one embodiment of catheter 10. The various dimensions shown in FIGS. 10(a) through 10(e) are merely illustrative, and are not intended to be limiting. Those skilled in the art, upon having read and understood this disclosure will understand and appreciate that other dimensions may be employed without departing from the scope of the inventions described and disclosed herein.

Figure 10A:
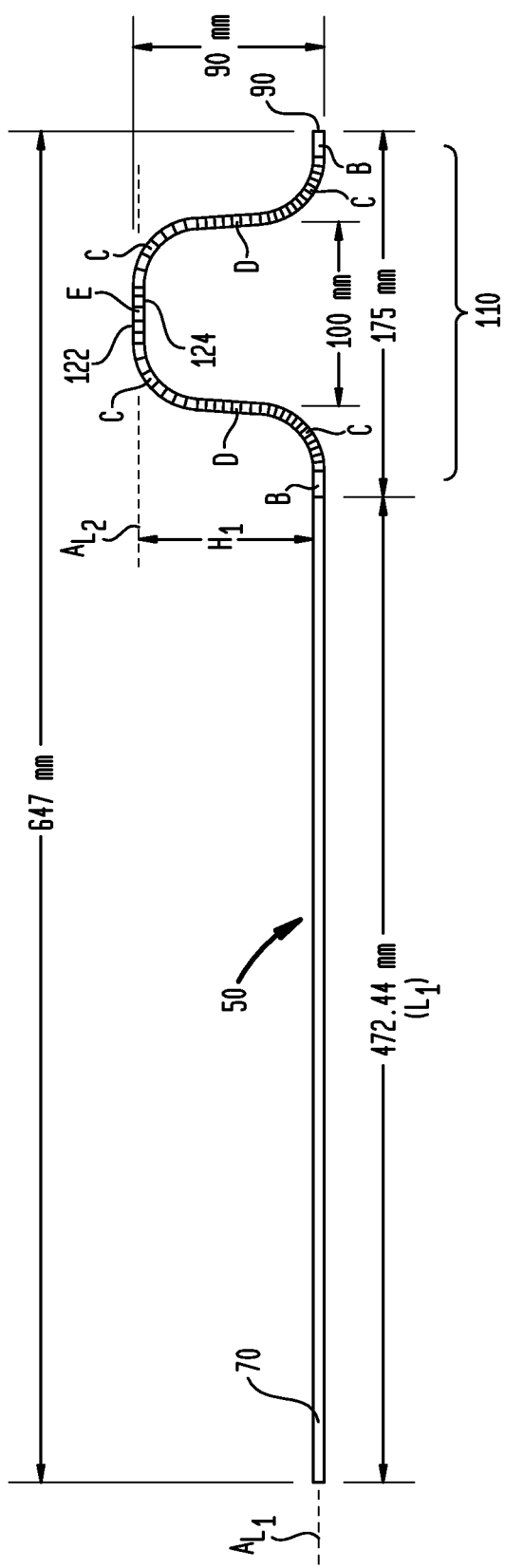
FIG. 10(a) shows a side view of still another embodiment of catheter body 50, proximal end 70, distal end 90 and distendable section 110 of an esophageal displacement and repositioning catheter 10.

FIG. 10(a) shows a side view of still another embodiment of catheter body 50, proximal end 70, distal end 90 and distendable section 110 of an esophageal displacement and repositioning catheter 10. For purposes of easing illustration, note that FIGS. 10(a) does not show catheter handle 30 (which would be included in any complete catheter 10). Also note that for purposes of easing illustration slots 131 are not shown on all portions of catheter 50 in FIG. 10(a), and that none of slots 131 shown in FIGS. 10(a) through 10(e) extend around the entire circumference of catheter body 50.

FIG. 10(b) shows a side view of catheter body 50 of esophageal displacement and repositioning catheter 10 shown in FIG. 10(a), including detail A thereof. As shown, slits or slots are cut or formed along catheter body 50, thereby imparting bendability to catheter body 10, which permits catheter body 10 to be inserted through patient's nose 240 or mouth 242, and then into patient's esophagus 200. Detail A in FIG. 10(b) shows that slits or slots 131 are cut or otherwise formed in catheter body 50 such that each slit or slot does not circumscribe the entire circumference of catheter body 50, and instead is formed or cut only through a prescribed range of the circumference; a matrix 133 of uncut material thus extends around and between slots or slits 131. Such a slot or slit configuration imparts a substantial degree of torsional rigidity to catheter 10 such that a rotation of proximal end 70 of catheter body 50 through a given number of degrees results in the same or substantially the same number of degrees of rotation at distal end 90 of catheter body 50. In some embodiments, and depending on the number, spacing, depth, width and length of the various slits or slots disposed along catheter body 50, a 1:1 ratio or essentially a 1:1 turn ratio can be provided between the proximal and distal ends 70 and 90 of catheter 50 as proximal end 70 of catheter 10 is rotated by a user in the patient's esophagus such that a health care provider can place distendable section 110 in an optimal position with respect to ablation site 310 (e.g., such that distendable section 110 bows or deflects outwardly and away from ablation site 310). Such positioning may be effected with the aid of fluoroscopy or other well-known medical imaging methods. According to some embodiments, the torsional rigidity of catheter 10 is provided by matrix 133 of solid and uncut or unslotted metal, metal alloy or similarly rigid material that extends between proximal and distal ends 70 and 90 of catheter body 10, where the matrix extends between and around slots or slits 131.

Detail A in FIG. 10(b) shows such a configuration of slots or slits, where merely by way of non-limiting illustrative example slots or slits 131 are spaced 1.02 mm apart in the longitudinal direction, and 1.25 mm apart in the axial direction, where slots or slits 131 are 0.11 mm wide, and matrix 133 extends and is disposed between such slots or slits 131. Those skilled in the art, upon having read and understood the present disclosure, will appreciate that numerous other configurations, dimensions, spacings and other characteristics of slots or slits 131 and matrix 133 may be employed to impart both bendability and torsional rigidity to catheter body 50. For example, slits or slots 131 may be spaced apart in the longitudinal direction from one another between about 0.5 mm and about 1.5 mm, may be spaced apart in the axial direction between about 0.75 mm and about 1.75 mm, and may be between about 0.05 mm and about 0.2 mm wide. Other spacings and widths are also contemplated.

Figure 10C:
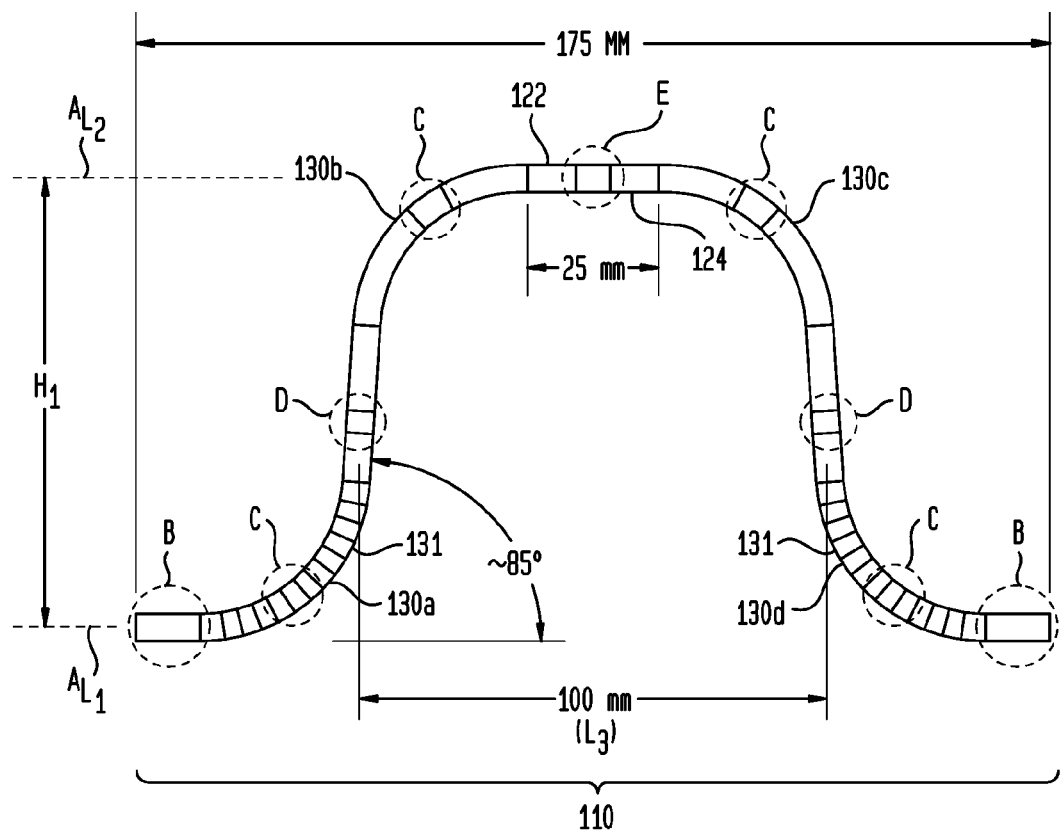
FIG. 10(c) shows a side view of distendable section 110 of esophageal displacement and repositioning catheter 10 shown in FIG. 10(a)
Figure 10D:
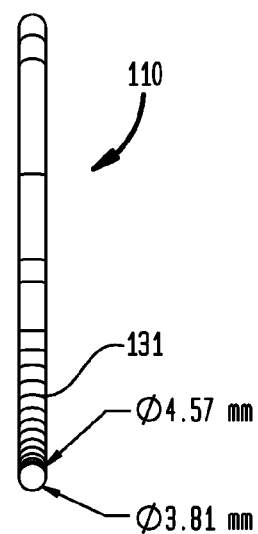
FIG. 10(d) shows an end view of distendable section 110 of esophageal displacement and repositioning catheter 10 shown in FIG. 10(c)

FIG. 10(c) shows a side view of distendable section 110 of esophageal displacement and repositioning catheter 10 shown in FIG. 10(a). FIG. 10(d) shows an end view of distendable section 110 of esophageal displacement and repositioning catheter 10 shown in FIG. 10(c). Details B, C, D and E are shown enlarged in FIG. 10(e). The various dimensions shown in FIGS. 10(a) through 10(e) are merely illustrative, and are intended to show only a few of many different embodiments.

The various dimensions of catheter body 50 and distendable section 110 shown in FIGS. 10(a) through 10(e) illustrate that according to some embodiments catheter body 50 has thin stainless steel walls approximately 0.76 mm thick (with an outer diameter of 4.57 mm, and an inner diameter of 3.81 mm—see FIG. 10(d). Spacing in the axial direction between slots or slits 131 (which can be 0.51 mm, by way of example) in joints 130a, 130b 130c and 130d is reduced relative to spacing in the axial direction between slots or slits 131 in other portions of distendable section 110 or catheter body 50 (which can be 0.64 mm, by way of example). Such variations in slot or slit spacing in the axial direction between adjacent slots or slits permits joints 130a, 130b, 130c and 130d to have increased bendability or flexibility relative to other portions of distendable section 110 and/or catheter body 50. This is required so that distendable section 110 can be deployed and distended with adequate curvature to move a patient's esophagus a safe distance away from ablation site 310.

The embodiment of catheter 10 shown in FIGS. 10(a) through 10(e) shares certain characteristics of the embodiments of catheters 10 (and certain portions thereof) shown in FIGS. 8(a) through 9(c). More particularly, those embodiments, and those shown in FIGS. 10(a) through 10(e), feature slits or slots cut into or otherwise formed in appropriate portions of thin-walled distendable section 110, which form bendable joints 130a, 130b, 130c and 130d, and that impart lesser flexibility or bendability to other portions of catheter body 50. Each such joint comprises one or slits cut through or into the sidewalls of distendable section 110, where the slits or slots are disposed at suitable locations along distendable section 110, and the slits or slots have suitable dimensions of depth, width and length to permit a desired amount, degree and type of bending at joints 130a, 130b, 130c and 130d. Moreover, and in one embodiment, slots or slits 131 are configured to act as range limiters at joints 13a, 130b, 130c and 130d so that such joints in distendable section 110 cannot be extended, or are difficult to extend, beyond prescribed ranges of bends (e.g., 85 degrees as shown in FIG. 10(c)). In one embodiment, slots or slits 131 have spacings and widths that permit limited maximum ranges of bending at joints 130a, 130b, 130c and 130d (e.g., about 85 degrees, although other degrees of bending are contemplated, such as about 90 degrees, about 80 degrees, about 70 degrees, about 60 degrees, about 50 degrees, about 45 degrees, about 40 degrees, about 30 degrees, and about 20 degrees).

In some embodiments joints 130a, 130b, 130c and 130d and other portions of distendable section 110 and/or catheter 50, are formed of thin-walled stainless steel or any other suitable metal, metal alloy, plastic or polymer. Thus, and while the disclosure with respect to FIGS. 8(a), 9(a) and FIGS. 10(a) through 10(e) focuses on an embodiment of catheter 10 where proximal end 50, catheter body 50, distendable section 110, and distal end 90 of catheter body 50 are formed of thin-walled medical grade stainless steel, it is to be understood that other suitable materials may also be employed to form catheter body 50.

Referring now to FIGS. 2(a) through 10(e), and according some embodiments, esophageal displacement catheter 10 comprises catheter body 50 comprising at least first lumen 40, distal end 90, proximal end 70, and distendable section 110. First lumen 40 extends between at least portions of proximal and distal ends 70 and 90 of catheter body 50. Catheter body 50 is configured to assume a substantially straight configuration along a first longitudinal axis $A_{L1}$, and/or to assume a flexible or limp configuration at least along portions thereof, when catheter body 50 is in a relaxed or non-active configuration. Catheter manipulation mechanism or handle 30 is disposed at or near proximal end 70 of catheter body 50. At least first pulling member 136 is disposed at least partially within catheter 10 and lumen 40, and has a distal portion thereof attached to a portion of catheter body 50 (e.g., first pulling member anchor 134) located at or near distal end 90 of catheter body 50. In one embodiment, pulling member 136 is operably connected to catheter manipulation mechanism 30 such that a user (e.g., a health care provider or physician) can tighten and relax pulling member 136 using, by way of non-limiting example, a pulling member tightening and loosening mechanism 34 forming a portion of or attached to catheter manipulation mechanism 30.

Distendable section 110 comprises a plurality joints, e.g., joints 130a, 130b, 130c and 130d, and is configured to permit distendable section 110 to deflect away from first longitudinal axis $A_{L1}$ and bend substantially within single plane 20 along plurality of joints 130 when pulling member 136 is pulled towards proximal end 70 of catheter body 50. Distendable section 110 and catheter body 50 are further configured to rotate substantially within single plane 20 when proximal end 70 of catheter body 50 is rotated by a user. Catheter body 50 is configured such that distendable section 110 is configured to assume a distended configuration suitable for displacing and repositioning esophagus 200 of patient 5 a suitable distance (e.g., at least 20 mm) away from patient's heart 220 when pulling member 136 is in an active or distended position within lumen 40 and catheter body 50 as pulling member 136 is tightened by the user manipulating catheter manipulation mechanism 30. Catheter 10 is configured such that a torsional and rotational force applied to proximal end 70 of catheter body 50 or to catheter manipulation mechanism 30 by the user results in a rotation of proximal end 70 of catheter body 50 through a prescribed angle determined by the user, which in turn results in the torsional force being transmitted efficiently through catheter body 50 and distendable section 110 such that distendable section 110 also rotates substantially through the same prescribed angle when the torsional and rotational force is applied.

In addition, the various embodiments of catheter 10 can feature one or more of the following characteristics. Distendable section 110 may comprise a plurality of substantially rigid segments (e.g., segments 112, 114, 116, 118 and 120) located in or on distendable section 110. Such segments can be serially connected to one another by flexible joints 130, where each joint 130 is rotatable through a prescribed range of angles. Such segments and joints may be configured to rotate together substantially within single plane 20 when proximal end 70 of catheter body 50 or catheter manipulation mechanism 30 is rotated by a user. One or more of joints 130 may have a range limiter 132 associated therewith. A range limiter 132 may be configured such that joint 130 associated therewith can bend no more than between about 40 degrees and about 90 degrees. Range limiters 132 may be formed a wire, a braided wire, a stranded wire, a synthetic fiber of high tensile strength, or any other suitable material. In one embodiment, plurality of joints 130 may comprise at least first, second, third, fourth, and fifth substantially rigid segments 112, 114, 116, 118 and 120 located in or on the distendable section 110.

In still other embodiments, catheter 10 can feature one or more of the following characteristics. Distendable section 110 may comprise a plurality of slots or slits 131 formed or machined therein, slots or slits 131 being configured to permit distendable section 110 to deflect away from first longitudinal axis $A_{L1}$ and bend substantially within single plane 20 along plurality of joints 130 when pulling member 136 is pulled towards proximal end 70 of catheter body 50, where joints 130 comprise slots or slits 131. Distendable section 110 and catheter body 50 may be configured to rotate substantially within single plane 20 when proximal end 70 of catheter body 50 or catheter manipulation mechanism 30 is rotated by the user. The plurality of joints 130 may further comprise at least first, second, third and fourth joints 130a, 130b, 130c, 130d, each of the first, second, third and fourth joints 130a, 130b, 130c, 130d together being rotatable through the prescribed angle. At least some of slots or slits 131 may be configured to act as range limiters 132 in distendable section 110. At least one of range limiters 132 may be configured such that the joint 130 associated therewith can bend no more than between about 40 degrees and about 90 degrees. First pulling member 136 may comprise one or more of a wire, braided wires, and stranded wires. Catheter 10 may further comprise a second pulling member 138 configured to cause elastic and/or deformable sheath 144 disposed at least around an outer diameter of distendable section 110 to engage a trailing edge 202 of patient 5's esophagus 200 when a proximal end of the second pulling member is pulled through the action of the user (e.g., by the user operating catheter manipulation mechanism 30). Distendable section 110 may comprise a polymeric or any other suitable material. At least portions of catheter body 50 may comprise thin-walled metal tubing. Such metal tubing may comprise stainless steel or alloys thereof. In some embodiments, the outside diameter of the metal tubing may range between about 2 mm and about 10 mm. One or more temperature sensors, ultrasonic transducers, navigation sensors, and/or radio opaque markers may be disposed in distendable section 110 or other portions of catheter body 50. At least one mark may be disposed along catheter body 50 that is indicative of at least one of a first position of distal end 90 of catheter body 50 in patient 5's esophagus 200 and a second position of distendable section 110 in patient 5's esophagus 200.

Figure 11:
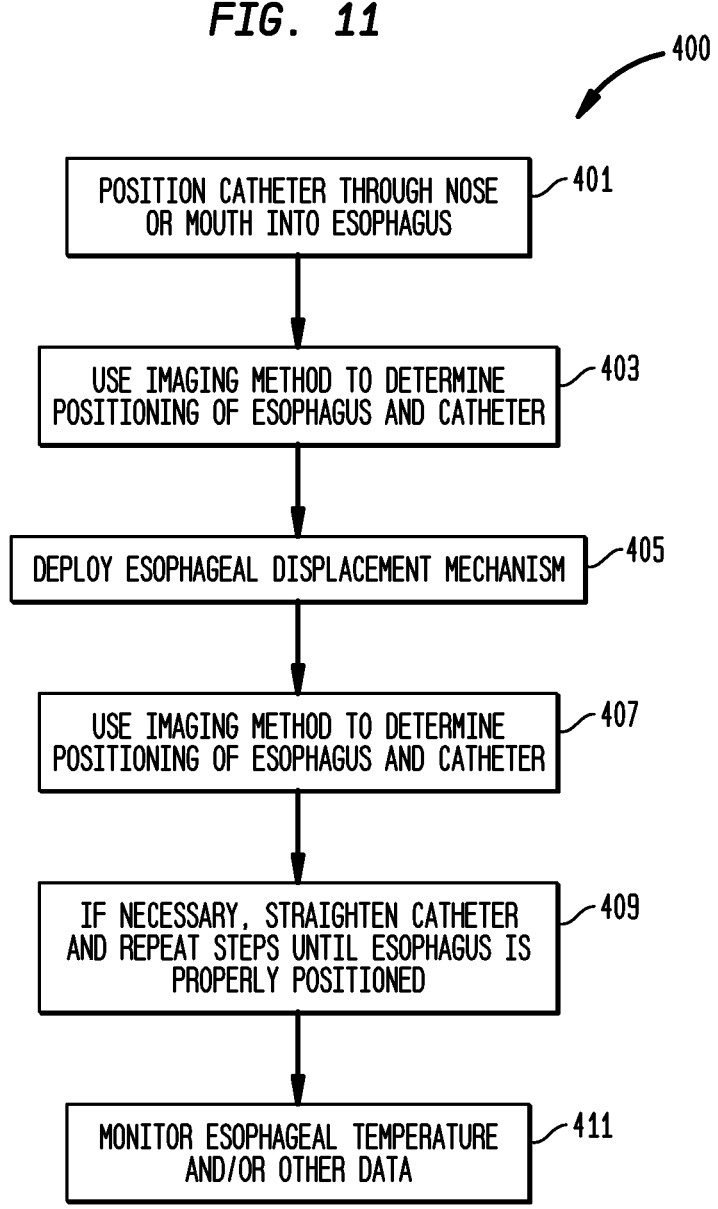
FIG. 11 shows one embodiment of a method for using an esophageal displacement and repositioning catheter.

FIG. 11 shows one embodiment of a method 400 for using an esophageal displacement and repositioning catheter 10. In FIG. 9, catheter 10 is first positioned through patient 5's nose or mouth at step 410. At step 403, a suitable imaging method is employed to determine the position of catheter 10 and distendable section 110 in esophagus 200 relative to heart 220. If catheter 10 is determined to be in an appropriate position in patient 5's esophagus relative to heart 220, at step 405 distension mechanism 110 of catheter 10 is deployed to reposition esophagus 200 away from heart 220 and/or ablation tip 310. At step 407, a suitable imaging method is once again employed to determine the position of catheter 10 and distendable section 110 in esophagus 200 relative to heart 220. If necessary, catheter 10 is straightened at step 409 and repositioned in esophagus 200. Temperature or other data can be acquired from catheter 10 in step 411, as described above.

Many variants, permutations and combinations of method 400 described above are contemplated, including methods where certain of the above-described steps are eliminated, steps practiced in an order different from that described above, or other steps are added.

In addition to the systems, devices, and components described above, it will now become clear to those skilled in the art that various methods associated therewith are also disclosed and contemplated, such as methods of manufacturing and modifying esophageal repositioning and displacement catheters.

Various aspects or elements of the different embodiments described herein may also be combined to implement esophageal repositioning and displacement techniques.

The foregoing outlines features of several embodiments so that those skilled in the art may better understand the detailed description set forth herein. Those skilled in the art will now understand that many different permutations, combinations and variations of esophageal repositioning and displacement catheters 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems in the use of esophageal repositioning and displacement catheters.

I claim:

1. An esophageal displacement catheter, comprising:
   a catheter body comprising at least one lumen, a distal end, a proximal end, a distendable section and sidewalls, the lumen extending between at least portions of the proximal and distal ends of the catheter body, the catheter body being configured to assume a substantially straight configuration along a longitudinal axis, or to assume a flexible or limp configuration along at least a portion of the longitudinal axis, when the catheter body is in a relaxed or non-active configuration;
   a catheter manipulation mechanism disposed at or near the proximal end of the catheter body;
   at least a first pulling member disposed at least partially within the catheter and the lumen and having a distal portion thereof attached to a portion of the catheter body located at or near the distal end of the catheter body, the first pulling member being operably connected to the catheter manipulation mechanism such that a user can tighten and relax the pulling member using a pulling member tightening and loosening mechanism forming a portion of or attached to the catheter manipulation mechanism, and
   a flexible deformable outer sheath or covering disposed over at least portions of the distendable section;
   wherein the distendable section comprises a plurality of substantially rigid sections and a plurality of joints having joint locations along the distendable section corresponding thereto, the rigid segments being connected to one another by the joints, the joints and rigid segments being configured to permit the distendable section to deflect away from the longitudinal axis and form a compound bend substantially within a single plane along the plurality of joints when the pulling member is pulled towards the proximal end of the catheter body, the distendable section and the catheter body further being configured to rotate substantially within the single plane when the proximal end of the catheter body is rotated by a user, the catheter body is configured such that the distendable section thereof is configured to assume a distended configuration between the proximal and distal ends of the catheter body, the distended configuration being suitable for displacing and repositioning an esophagus of a patient at least 20 mm away from the patient's heart when the pulling member is in an active or retracted position as the pulling member is tightened by the user manipulating the catheter manipulation mechanism, the catheter is configured such that a torsional and rotational force applied to the proximal end of the catheter body or the catheter manipulation mechanism by the user resulting in a rotation of the proximal end of the catheter body through a prescribed angle determined by the user results in the torsional force being transmitted through the catheter body and the distendable section such that the distendable section also rotates substantially through the prescribed angle when the torsional and rotational force is applied, and the distendable section comprises a plurality of openings disposed in the sidewalls of the catheter body at or near at least some of the joint locations such that portions of the first pulling member extend through the openings and become located outside the lumen and the catheter body when the first pulling member is placed in the active or retracted position, the flexible sheath being configured to cover the openings and become deformed and distended by portions of the pulling member located outside the catheter body and the lumen when the first pulling member is in the active or retracted position.

2. The esophageal displacement catheter of claim 1, wherein each joint is rotatable through a prescribed range of angles.

3. The esophageal displacement catheter of claim 1, wherein the segments and joints are configured to rotate together substantially within the single plane when the proximal end of the catheter body or catheter manipulation mechanism is rotated by a user.

4. The esophageal displacement catheter of claim 1, wherein at least one of the joints has a range limiter associated therewith.

5. The esophageal displacement catheter of claim 4, wherein at least one of the range limiters is configured such that the joint associated therewith can bend no more than between about 40 degrees and about 90 degrees.

6. The esophageal displacement catheter of claim 4, wherein the range limiter is one of a wire, a braided wire, a stranded wire, and a synthetic fiber of high tensile strength.

7. The esophageal displacement catheter of claim 1, wherein the plurality of substantially rigid segments further comprises at least first, second, third, fourth, and fifth segments, the first and second segments being connected to one another by a first joint configured to rotate a first angle substantially within the single plane, the second and third segments being connected to one another by a second joint configured to rotate a second angle substantially within the single plane, the third and fourth segments being connected to one another by a third joint configured to rotate a third angle substantially within the single plane, the fourth and fifth segments being connected to one another by a fourth joint configured to rotate a fourth angle substantially within the single plane, each of the second, third and fourth segments being rotatable through the second, third and fourth joints through the first, second, third and fourth angles.

8. The esophageal displacement catheter of claim 1, wherein the distendable section comprises a plurality of slots or slits formed or machined therein, the slots or slits being configured to permit the distendable section to deflect away from the first-longitudinal axis and bend substantially within the single plane along the plurality of joints when the pulling member is pulled towards the proximal end of the catheter body, the joints comprising the slots or slits.

9. The esophageal displacement catheter of claim 8, wherein the distendable section and the catheter body are configured to rotate within substantially the single plane when the proximal end of the catheter body or the catheter manipulation mechanism is rotated by the user.

10. The esophageal displacement catheter of claim 8, wherein the plurality of joints further comprises at least first, second, third and fourth joints, each of the first, second, third and fourth joints together being rotatable through the prescribed angle.

11. The esophageal displacement catheter of claim 8, wherein at least some of the slots or slits are configured to act as range limiters in the distendable section.

12. The esophageal displacement catheter of claim 11, wherein at least one of the range limiters is configured such that the joint associated therewith can bend no more than between about 40 degrees and about 90 degrees.

13. The esophageal displacement catheter of claim 1, wherein the first pulling member comprises one or more of a wire, braided wires, and stranded wires.

14. The esophageal displacement catheter of claim 1, wherein the sheath is further configured to be distended by a second pulling member to engage a trailing edge of the patients esophagus when a proximal end of the second pulling member is tightened or retracted.

15. The esophageal displacement catheter of claim 1, wherein at least the distendable section comprises a polymeric material.

16. The esophageal displacement catheter of claim 1, wherein at least portions of the catheter body comprise thin-walled metal tubing.

17. The esophageal displacement catheter of claim 1, wherein the recesses or holes are located opposite the joints of the distendable section.

18. The esophageal displacement catheter of claim 1, wherein a diameter of the catheter body ranges between about 4 mm and about 10 mm.

19. The esophageal displacement catheter of claim 1, further comprising one or more temperature sensors disposed in the distendable section.

20. The esophageal displacement catheter of claim 1, further comprising one or more ultrasonic transducers disposed in the distendable section.

21. The esophageal displacement catheter of claim 1, further comprising one or more navigation sensors disposed in the distendable section.

22. The esophageal displacement catheter of claim 1, further comprising one or more radio opaque markers disposed in the distendable section.

23. The esophageal displacement catheter of claim 1, further comprising at least one mark disposed along the catheter body indicative of at least one of a first position of the distal end of the catheter in the patient's esophagus and a second position of the distendable section in the patients esophagus.

24. A method of displacing a portion of an esophagus of a patient away from the patients heart with an esophageal displacement catheter, the catheter comprising a catheter body comprising at least one lumen, a distal end, a proximal end, a distendable section and sidewalls, the lumen extending between at least portions of the proximal and distal ends of the catheter body, the catheter body being configured to assume a substantially straight configuration along a first longitudinal axis, or to assume a flexible or limp configuration along at least a portions of the longitudinal axis, when the catheter body is in a relaxed or non-active configuration, a catheter manipulation mechanism disposed at or near the proximal end of the catheter body, at least a first pulling member disposed at least partially within the catheter and the lumen and having a distal portion thereof attached to a portion of the catheter body located at or near the distal end of the catheter body, the pulling member being operably connected to the catheter manipulation mechanism such that a user can tighten and relax the pulling member using a pulling member tightening and loosening mechanism forming a portion of or attached to the catheter manipulation mechanism, and a flexible deformable outer sheath or covering disposed over at least portions of the distendable section, wherein the distendable section comprises a plurality of substantially rigid sections and a plurality of joints having joint locations along the distendable section corresponding thereto, the segments being connected to one another by the joints, the joints and rigid segments being configured to permit the distendable section to deflect away from the longitudinal axis and form a compound bend substantially within a single plane along a plurality of joints when the pulling member is pulled towards the proximal end of the catheter body, the distendable section and the catheter body further being configured to rotate within substantially the single plane when the proximal end of the catheter body is rotated by a user, and the catheter body is configured such that the distendable section thereof is configured to assume a distended configuration between the proximal and distal ends of the catheter body, the distended configuration being suitable for displacing and repositioning an esophagus of a patient at least 20 mm away from the patients heart when the pulling member is in an active or retracted position as the pulling member is tightened by the user manipulating the catheter manipulation mechanism, the catheter is configured such that a torsional and rotational force applied to the proximal end of the catheter body or the catheter manipulation mechanism by the user resulting in a rotation of the proximal end of the catheter body through a prescribed angle determined by the user results in the torsional force being transmitted through the catheter body and the distendable section such that the distendable section also rotates substantially through the prescribed angle when the torsional and rotational force is applied, and the distendable section comprises a plurality of openings disposed in the sidewalls of the catheter body at or near at least some of the joint locations such that portions of the first pulling member become located outside the lumen and the catheter body when the first pulling member is placed in the active or retracted position, the flexible sheath being configured to cover the openings and portions of the pulling member located outside the catheter body and the lumen when the first pulling member is in the active or retracted position, the method comprising:

inserting the distal end of the catheter body in the patients nose or mouth;

inserting and positioning the distal end of the catheter into the patient's esophagus, and causing the first pulling member to retract in the direction of the proximal end of the catheter body such that the distendable section is deployed, the distendable section assumes the distended configuration, and the distendable section positions the patient's esophagus away from the patients heart.

25. The esophageal displacement method of claim 24, further comprising medically imaging the position of the catheter in the patients esophagus.

26. The esophageal displacement method of claim 25, further comprising re-positioning the catheter in the patients esophagus based on the imaging results.

27. The esophageal displacement method of claim 24, further comprising monitoring a temperature of a trailing edge of the patients esophagus using one or more temperature sensors located in the distendable section of the catheter.

* * * * *